US007863267B2

(12) United States Patent  
Legarda Ibanez

(10) Patent No.: US 7,863,267 B2
(45) Date of Patent: *Jan. 4, 2011

(54) USE OF SELECTIVE CHLORIDE CHANNEL MODULATORS TO TREAT METHAMPHETAMINE ABUSE

(75) Inventor: Juan Jose Legarda Ibanez, Madrid (ES)

(73) Assignee: Hythiam, Inc., Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/119,911

(22) Filed: May 13, 2008

(65) Prior Publication Data

US 2008/0207599 A1 Aug. 28, 2008

Related U.S. Application Data

(63) Continuation of application No. 11/111,435, filed on Apr. 21, 2005, which is a continuation-in-part of application No. 10/621,229, filed on Jul. 15, 2003, now Pat. No. 7,348,321, which is a continuation-in-part of application No. 10/622,068, filed on Jul. 15, 2003, now Pat. No. 7,186,711.

(51) Int. Cl.
*A61K 31/55* (2006.01)
*A61K 31/19* (2006.01)

(52) U.S. Cl. ...................... 514/220; 514/557
(58) Field of Classification Search .................. 514/220
See application file for complete search history.

(56) References Cited

U.S. PATENT DOCUMENTS

| 5,028,611 A | 7/1991 | Halikas |
| 5,229,120 A | 7/1993 | DeVincent |
| 5,385,903 A * | 1/1995 | Steppuhn et al. ............ 514/249 |
| 5,434,156 A | 7/1995 | Bjork et al. |
| 5,519,017 A | 5/1996 | Opitz |
| 6,346,528 B1 | 2/2002 | Yelle |
| 6,451,783 B1 | 9/2002 | Hadcock et al. |
| 6,541,520 B1 | 4/2003 | Dewey et al. |
| 6,593,367 B1 | 7/2003 | Dewey et al. |
| 6,890,951 B2 | 5/2005 | Dewey et al. |
| 6,906,099 B2 | 6/2005 | Dewey et al. |
| 7,186,711 B2 | 3/2007 | Ibanez |
| 7,348,321 B2 | 3/2008 | Ibanez |
| 2002/0150632 A1 | 10/2002 | Scott |
| 2004/0162322 A1 | 8/2004 | Rosenbaum |
| 2005/0192271 A1 | 9/2005 | Ibanez |
| 2006/0167723 A1 | 7/2006 | Berg |

FOREIGN PATENT DOCUMENTS

| WO | 99/61014 | 5/1999 |
| WO | WO 2006/110557 A2 | 10/2006 |
| WO | WO 2006/110580 A2 | 10/2006 |
| WO | WO 2006/110642 A2 | 10/2006 |

OTHER PUBLICATIONS

Moy et al.; "Enhanced ultrasonic vocalization and Fos protein expression following ethanol withdrawal: effects of flumazenil"; 2000; Psychopharmacology; 105: 208-215.*
Anglin et al.; "History of the methamphetamine problem"; 2000; Journal of Psychoactive Drugs; 32(2): 137-41.*
Klotz, et al.; Pharmacokinetics and Clinical Use of Flumazenil; 1988; Clinical Pharmacokinetics; 14(1): 1-12.*
Gerra et al.; "Intravenous flumazenil versus oxazepam tapering in the treatment of benzodiazepine withdrawl: a randomized, placebo-controlled study"; 2002; Addiction Biology; 7; 385-395.*
Aguirre et al. Plasma b-endorphin levels in chronic alcoholics, Alcohol, vol. 7, pp. 409-412, 1990.
Derlet, Robert W. et al.; "Flumazenil Induces Seizures and Death in Mixed Cocaine-Diazepam Intoxications"; Annals of Emergency Medicine, vol. 23, No. 3, Mar. 1994, pp. 494-498.
Derlet, R.W. et al.; "Anticonvulsant Modification of Cocaine-Induced Toxicity in the Rat"; Neuropharmacology, vol. 29, No. 3, pp. 255-259, 1990.
Gasior et al. Chlormethiazole: Effectiveness against Toxic Effects of Cocaine in Mice. The Journal of Pharmacology and Experimental Therapeutics. vol. 295, No. 1, pp. 153-161. Oct., 2000.
Ito, Kouichi; "The Role of Gamma-aminobutyric Acid (GABA)-Benzodiazepine Neurotransmission in an Animal Model of Methamphetamine-Induced Psychosis"; Hokkaido J. Med Sci 74(2), pp. 135-144, 1999 (English Abstract Only).
Ito, K. "The Role of Benzodiazepine Receptors in the Acquisition and Expression of Behavioral Sensitization to Methamphetamine"; Pharmacology Biochemistry and Behavior, vol. 65, No. 4, pp. 705-710, 2000.
Malbrain et al.; "A Massive, Near-Fatal Cocaine Intoxication in a Body-Stuffer"; Acta Clinica Belgium 49.1 (1994), pp. 12-18.
Soderpalm et al. Benzodiazepines enhance the consumption and palatability of alcohol in the rat. Psychopharmacology, 1998, 137:215-222.
Uki, F. et al.; "The effect of flumazenil administration on acute cocaine intoxication of rats"; Arukoru Kenkyuto Yakubutsu Ison; Apr. 1994, 29(2):92-102 (Abstract only).
Woolf, Alan; "Cocaine Poisoning"; Clinical Toxicology Review, vol. 18, No. 8, May 1995; pp. 1-6.
Drug Facts and Comparsions 1997 Edition, pp. 3373-3379.
Non-final Office Action, U.S. Appl. No. 11/615,460, mailed May 13, 2010.
Final Office Action, U.S. Appl. No. 11/111,435, mailed Dec. 8, 2009.
Response and Request for Continued Examination, U.S. Appl. No. 11/11,435, filed Jun. 30, 2010.

* cited by examiner

*Primary Examiner*—Brandon J Fetterolf
*Assistant Examiner*—Timothy P Thomas
(74) *Attorney, Agent, or Firm*—Kilpatrick Stockton, LLP

(57) ABSTRACT

The invention relates to methods of and treatments for using pharmaceutical compositions from a class of compounds that directly or indirectly selectively modulates $GABA_A$ chloride channel activity to treat alcohol and/or stimulant substance abuse. The present invention also relates to methods of, and protocols for, relieving symptoms associated with alcohol and/or stimulant substance abuse in a comprehensive treatment plan. More specifically, the present invention relates to the use of a selective chloride channel modulator, such as flumazenil, to treat alcohol and/or psychostimulant dependency, the withdrawal symptoms associated therewith, and the cravings associated therewith.

7 Claims, 6 Drawing Sheets

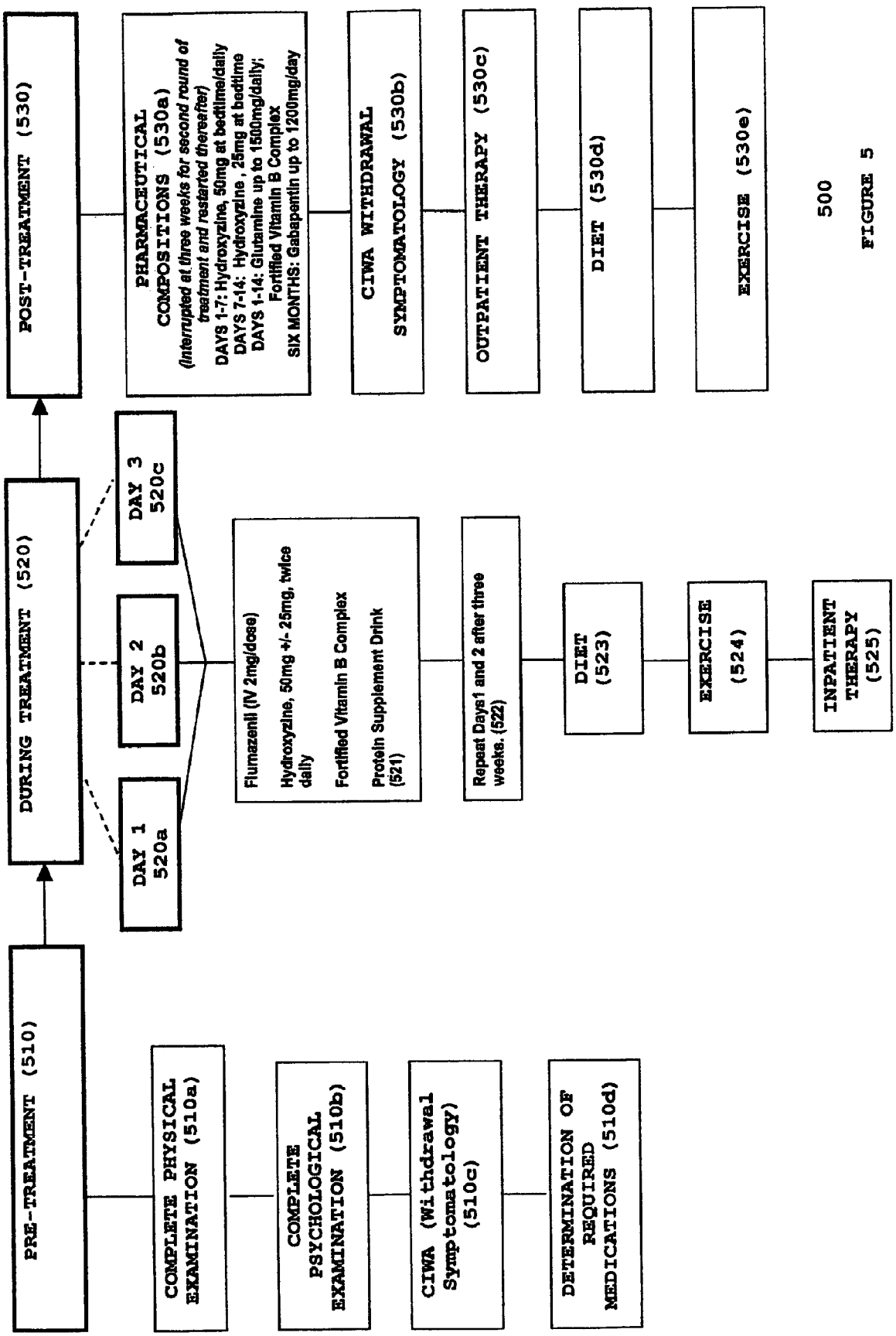

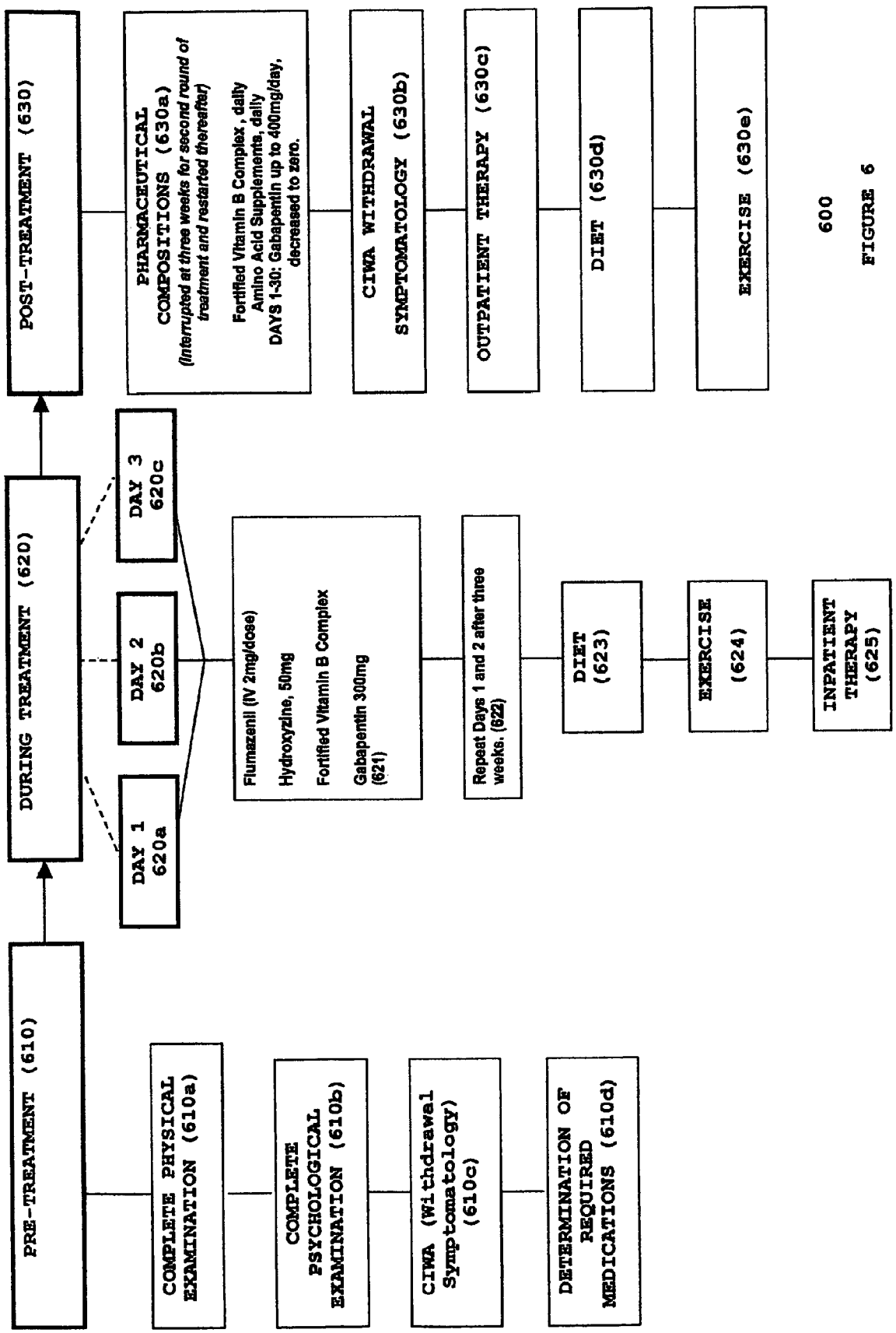

USE OF SELECTIVE CHLORIDE CHANNEL MODULATORS TO TREAT METHAMPHETAMINE ABUSE

RELATED APPLICATIONS

This application is a continuation of U.S. application Ser. No. 11/111,435, filed Apr. 21, 2005, which is a continuation-in-part of U.S. patent application Ser. No. 10/621,229, filed on Jul. 15, 2003, now U.S. Pat. No. 7,348,321, which claims priority to PCT Application No. PCT/ES02/00008, filed Jan. 10, 2002, and Spanish Provisional Application P200100106, filed Jan. 17, 2001, each herein incorporated by reference in its entirety; and which is a continuation-in-part of U.S. patent application Ser. No. 10/622,068, filed on Jul. 15, 2003, now U.S. Pat. No. 7,186,711, which claims priority to PCT Application No. PCT/ES02/00061, filed Feb. 8, 2002, and Spanish Provisional Application P200100342, filed Feb. 15, 2001, each herein incorporated by reference in its entirety.

FIELD OF THE INVENTION

The invention relates to methods of, and methodologies for, using pharmaceutical compositions from a class of compounds that directly or indirectly selectively modulates $GABA_A$ chloride channel activity to treat alcohol and/or psychostimulant substance abuse, including, but not limited to, the various physical and psychological states that manifest an individual's impaired control over substance use, addiction, continued substance use despite harm, compulsive substance use, cravings, psychological dependence, physical dependence, tolerance, a maladaptive pattern of substance use, preoccupation with substance use, and/or the prevalence of withdrawal symptoms upon cessation of use. The present invention also relates to methods of, and systems for, relieving symptoms associated with said alcohol and stimulant substance abuse in a comprehensive treatment plan. More specifically, the present invention relates to the use of a compound, such as flumazenil, to treat alcohol and/or psychostimulant substance abuse, the withdrawal symptoms associated therewith, and the cravings associated therewith.

BACKGROUND OF THE INVENTION

Alcohol and stimulant substance abuse disorders have a devastating economic and societal impact on the United States population. Alcohol and stimulant substance dependency is a multi-factorial neurological disease. The use of such drugs impacts an array of neurotransmission circuits in the brain, with a suggested final common pathway of activation of the mesolimbic reward circuit that is mediated via enhanced dopamine release. Over time, repeated exposure to these drugs causes modification of the neurotransmission circuits and adaptations in post-receptor signaling cascades. The effects of this neuronal modification are twofold. First, a reduction in the ability of natural rewards to activate the reward pathways leads to depressed motivation and mood, and increased compulsion to take more drugs. Second, there is a production of long-lasting memories related to the drug experience that, when stimulated by stressful events or exposure to drug-associated or mood-associated cues, act to stimulate cravings for the drug.

For many individuals, an innate neurochemical anomaly renders them susceptible to substance dependency or addictive behavior, even before any long-term effects of alcohol on neurological processing are evident. It is clear, however, that excessive drinking over time can lead to the impairment of brain function and result in structural brain changes in frontal and prefrontal areas of the brain, which are associated with cognition. Impaired cognition and judgment can therefore become permanent.

Alcohol affects the mesolimbic dopamine circuit by modifying the activity of two key receptors in the dopamine circuit, the $GABA_A$ receptor and NMDA receptor. GABA (gamma-aminobutryic acid) is a neurotransmitter that is a predominant inhibitory transmitter in areas of the brain such as the cortex and basal ganglia. The NMDA (N-methyl-D-aspartate) receptor is a ligand-gated ionic channel activated by and involved in the release of the neurotransmitter glutamate, which is an important excitatory transmitter in the brain. The positive affect on the mesolimbic dopamine circuit creates a self-reinforcing cycle of neuropathophysiological reward that drives individuals to become alcohol dependent. Alcohol increases chloride channel ion flow, relative to the post-synaptic chloride channel at rest, by engaging a $GABA_A$ receptor site. Benzodiazepines have a similar affect.

Acute exposure to alcohol results in the up regulation of NMDA and down regulation of the GABA-ergic system. Repeated exposure results in cross-tolerance and cross-dependence between alcohol and benzodiazepines. Consequently, an alcohol dependent person experiences stress, a down regulation of $GABA_A$ and an increase in the severity of withdrawal symptoms when he or she attempts to withdraw.

Therefore, when an alcoholic attempts to initiate abstinence or stop consuming alcohol, he or she may experience withdrawal symptoms, including cravings, which often result in a failure to stop consuming alcohol. Traditional alcohol withdrawal symptoms include anxiety, tremors, difficulty sleeping, elevated pulse and blood pressure, nausea, and vomiting. In some cases, withdrawal symptoms may be more severe and result in complications, including seizures, hallucinosis, hallucinations with severe tremors (or "delirium tremens", DTs) and difficulty regulating body temperature. These complications may often be fatal. In an exemplary case, withdrawal symptoms begin appearing 6 to 12 hours after a prior consumption of alcohol. Alcohol withdrawal syndrome may occur 6 to 48 hours after a prior consumption of alcohol.

Psychostimulants are a class of central nervous system stimulants and include cocaine, crack cocaine, ephedrine, amphetamines, such as dextroamphetamine (commonly referred to as amphetamine), methamphetamine, and phenmetrazine, methylenodioxyamphetamine (MDA), and methylenodioxymethamphetamine (MDMA or "ecstasy"), and analogs thereof. Amphetamine-like drugs are classified as indirect action agonists of noradrenergic, dopaminergic, and serotonergic synapses which result from inhibiting both neurotransmitters reuptake and the enzyme monoamine oxidase (MAO). They are competitive inhibitors of noradrenaline and dopamine transport and, in high doses, also inhibit serotonin reuptake. They cause non-calcium dependent dopamine and noradrenaline release.

Stimulants affect a number of neurological circuits, including dopaminergic, beta-adrenergic, serotonergic, glutamatergic, GABAergic circuits, and ultimately results in impaired dopamine function. $GABA_A$ functionality is eventually impaired.

At lower doses, stimulants result in a feeling of euphoria, an increase in energy, a decrease in fatigue, and an increase in mental acuity. As dosing increases, a person starts to experience tremors, emotional instability, restlessness, irritability, and feelings of paranoia and panic. At higher doses, a person experiences intense anxiety, paranoia, hallucinations, hypertension, tachycardia, hyperthermia, respiratory depression, heart failure, and seizures.

Traditional withdrawal symptoms for those trying to end their abuse of psychostimulants include: depressed mood, fatigue, vivid and unpleasant dreams, difficulty sleeping or excessive sleeping, increased appetite, anxiety, and agitation. Cravings for the psychostimulant are particularly pronounced and may recur for many months, if not years. A return of "normal" mood and the ability to experience pleasure may take a significant amount of time due to the depletion or modification of neurotransmitters.

Alcohol and psychostimulant substance abuse are often associated with changes in food selection and intake that lead to calorie and protein malnutrition and disruption of energy expenditure. The resulting malnutrition is related to deficient food intake, malabsorption, increased protein turnover, liver disease, intensity of drug addiction, anorexia, and poor food and drink consumption. Furthermore, the disturbance of social and familial links can itself result in poor nutrition. Malnutrition, in turn, is associated with impairment of immune function. Therefore, restoration and maintenance of normal physiological function can be regarded as an important objective when treating substance dependencies. Effective treatment of alcohol substance abuse should address the neurological, nutritional, and psychosocial disturbances that both cause and exacerbate the abuse.

The customary treatment of alcohol dependency includes the administration of vitamin B and C complexes, benzodiazepines (to calm agitation and blunt withdrawal symptoms), and, sometimes, disulfuram (to prevent alcohol use). The traditional medical detoxifications involve replacing alcohol with substances pharmacologically similar to alcohol in order to reduce withdrawal agitation. Detoxification can take 3-5 days, involves sedation with potentially dependence forming drugs, and is generally uncomfortable for the patient.

Traditional treatments for managing withdrawal and craving for alcohol and/or psychostimulants (such as cocaine) may include the administration of benzodiazepines (e.g. lorezepam) if agitation or anxiety is present, antidepressants to treat persistent depression and dopamine-agonists to increase brain dopamine. These treatments, however, have limited success and have high dropout rates. Dropout can refer to several different types of treatment events related to the premature cessation of treatment, including times when patients dropout during treatment and when patients relapse following treatment.

A review of the various pharmacological treatments existing for the treatment of alcohol dependency can be found in A Practice Guideline for the Treatment of Patients With Substance Use Disorders Alcohol, Cocaine and Opioids, produced by the Work Group on Substance Use Disorders of the American Psychiatric Association and published in Am. J. Psychiatry 152:11, November 1995 Supplement. An updated review of the treatment of alcohol dependency was created by Mayo-Smith et al., JAMA Jul. 9, 1997, Vol. 278, No. 2, who conclude by indicating that the benzodiazepines (alprazolam, diazepam, halazepam, lorazepam or oxazepam) are agents suitable for the treatment of alcohol dependency, whereas beta-blockers (propranolol), neuroleptics (chlorpromazine and promazine), clonidine and carbamazepine, may be used in coadjuvant therapy, but their use is not recommended as a monotherapy. A benzodiazepine is any of a group of chemically similar psychotropic drugs with potent hypnotic and sedative action, used predominantly as anti-anxiety (anxiolytic) and sleep-inducing drugs. Side effects of these drugs may include impairment of psychomotor performance; amnesia; euphoria; dependence; and rebound (i.e., the return of symptoms) transiently worse than before treatment, upon discontinuation of the drug.

In certain conventional uses, flumazenil, an imidazobenzodiazepine derivative, antagonizes the actions of benzodiazepines on the central nervous system. In conventional doses, flumazenil [ethyl 8-fluoro-5,6-dihydro-5-methyl-6-oxo-4H-imidazol[1,5-a][1,4]benzodiazepine-3-carboxylate] therefore acts as a benzodiazepine antagonist which selectively blocks the effects exerted on the central nervous system via the benzodiazepine receptors. This active principle is indicated to neutralize the central sedative effect of the benzodiazepines; consequently, it is conventionally used in anesthesia to end the general anesthesia induced and maintained with benzodiazepines in hospitalized patients, or to stop the sedation produced with benzodiazepines in patients undergoing brief diagnostic or therapeutic procedures on an inpatient or outpatient basis.

Some clinical studies have examined the role of flumazenil in the reversal of alcohol withdrawal syndrome. Gerra et al., 1991, Current Therapeutic Research, Vol. 50, 1, pp 62-66, describe the administration to 11 selected alcoholics (who did not have cirrhosis, metabolic disorders, convulsions, addictions to other substances or psychiatric disorders) of 2 mg/day of flumazenil divided into 4 doses (0.5 mg), intravenously (IV) via a continuous drip, in saline solution, every 6 hours for 48 hours. The use of 0.5 mg of flumazenil is based on the presentation of pharmaceutical preparations that contain said active principle but not on studies performed in humans concerning the level of occupation of the receptors involved. The flumazenil was administered at the rate of 0.5 mg of flumazenil every 6 hours (i.e., 0.08 mg/hour of flumazenil). The tests performed by Gerra et al. present some characteristics that are far from the actual circumstances, for example, the tests were performed on a small sample (11 individuals) of select patients not representative of the pathology considered since it is relatively customary that these patients may have cirrhosis, metabolic disorders, addictions to other substances (cocaine, heroin, etc.) and/or psychiatric disorders. Moreover, Gerra et al. do not present data concerning the evaluation of dependency or craving either before or after administration of the drug. Most importantly, however, Gerra et al. discloses the administration of very small quantities of flumazenil over long periods of time, which was not particularly effective at treating alcohol dependency.

Nutt et al. [Alcohol & Alcoholism, 1993, Suppl. 2, pp 337-341. Pergamon Press Ltd.; Neuropschychopharmacology, 1994, Vol. 10, 35, part 1, Suppl., p. 85f) describe the administration to 8 alcoholics in the acute withdrawal phase of 2 mg of flumazenil, by IV, for 1 minute. The results obtained after the administration of flumazenil were not completely satisfactory since in some cases, there was an immediate worsening of the withdrawal symptoms, especially of sweats and anxiety. In other cases, the withdrawal symptoms disappeared but returned a few hours later. Since flumazenil is metabolized and eliminated very rapidly, the IV administration of a relatively high dose of flumazenil in a single dose of 2 mg, for 1 minute, has several disadvantages since such dosing triggers undesired side effects, and the bulk of flumazenil administered yields no pharmacological response and results in unnecessary expense.

Moreover, the results obtained by Gerra et al. and by Nutt et al. are not conclusive since in some cases, no significant changes were observed in either the blood pressure or the heart rate of patients after the administration of flumazenil, an immediate worsening of the withdrawal symptoms was observed, especially sweats and anxiety, and the tests were performed using a very small non-representative patient sample.

In two articles by Sheryl S. Moy (Skipper Bowles Center for Alcohol Studies, Department of Psychiatry and UNC Neuroscience Center), investigators disclose the use of flumazenil to block anxiety created by ethanol withdrawal in rats. According to Moy et al. (2000), in rat models of the ethanol withdrawal syndrome, flumazenil can reverse anxiogenic withdrawal effects such as inhibition during a social interaction test (File et al. 1989, 1992) and reduced open arm exploration on an elevated plus maze (Moy et al. 1997) Further in Moy et al. (2000) and Uzbay et al. (1995) it was reported that flumazenil could prevent the agitation and stereotyped behavior induced by withdrawal from long-term ethanol exposure in rats. Doses, however, were provided for rat models and cannot be readily translated to human dosage levels. Moreover, the prior art teaches the use of flumazenil in a conventional benzodiazepine treatment model, which requires the substitution of ethanol usage with large quantities of benzodiazepine to alleviate withdrawal symptoms.

However, all disclosed uses of flumazenil in the treatment of alcohol withdrawal and addiction have relied on either the single administration of large quantities of flumazenil or on-going administrations of very low quantities of flumazenil over long periods of time. Moreover, the disclosed administrative regimens has not applied the use of flumazenil, or a class of compounds represented by flumazenil, for treating psychostimulant substance abuse at all. Furthermore, conventional treatments for alcohol and/or psychostimulant dependency have had limited success and often have undesirable side effects. New approaches are needed that can improve treatment outcomes and reduce the risk of relapse. Thus, an improved treatment methodology for treating alcohol and/or psychostimulant substance abuse is desirable.

In addition, conventional treatments for controlling withdrawal symptoms and cravings for alcohol and/or psychostimulants have had limited success and often have undesirable side effects. Thus, an improved treatment methodology for controlling cravings and withdrawal symptoms caused by alcohol and/or psychostimulant substance abuse would be desirable.

It would also be desirable to have an improved methodology and protocol for treating alcohol and/or psychostimulant substance abuse, which results in reduced patient dropout rates.

SUMMARY OF THE INVENTION

The present invention is directed towards various methods and protocols for the treatment of alcohol and/or psychostimulant substance abuse based on safe and effective administration of a class of compounds that directly or indirectly selectively modulates $GABA_A$ chloride channel activity, such as, but not limited to flumazenil, and which requires a short period of time to effectively eradicate symptoms of alcohol and/or psychostimulant substance abuse. As defined herein, the class of compounds that selectively modulates $GABA_A$ chloride channel activity (referred to herein as Selective Chloride Channel Modulators) is intended to cover the selective modulation of chloride channel activity and does not encompass full agonists of the $GABA_A$ receptor, such as fluoxetine benzodiazpenes. Additionally, as defined herein, the term substance abuse is used to refer to the various physical and psychological states that manifest an individual's impaired control over alcohol and/or stimulant substance use, continued alcohol and/or stimulant substance use despite harm, addiction, compulsive alcohol and/or stimulant substance use, cravings, psychological dependence, physical dependence, tolerance, a maladaptive pattern of alcohol and/or stimulant substance use, preoccupation with alcohol and/or stimulant substance use, and/or the prevalence of withdrawal symptoms upon cessation of use.

It is another object of the present invention to provide for methods and protocols for the treatment of alcohol and/or psychostimulant substance abuse that includes administration, to a patient in need of said treatment, of a therapeutically effective quantity of a compound that directly or indirectly selectively modulates chloride channel activity, administered in multiple doses at a predetermined rate, until said therapeutically effective quantity to treat alcohol and/or psychostimulant substance abuse has been reached.

It is another object of the present invention to provide for methods and protocols that reduce cravings and withdrawal symptoms from addiction to alcohol and/or psychostimulants that includes administration, to a patient in need of said treatment, of a therapeutically effective quantity of a compound that directly or indirectly selectively modulates chloride channel activity, administered in multiple doses at a predetermined rate, until said therapeutically effective quantity administration reduces cravings and withdrawal symptoms from addiction to alcohol and/or psychostimulants.

It is another object of the present invention to provide a methodology for controlling cravings, reducing withdrawal symptoms and treating addiction to alcohol and/or psychostimulants. It is yet another object of the present invention to administer a compound that directly or indirectly selectively modulates chloride channel activity, such as, but not limited to flumazenil, in a therapeutically effective quantity so as to control cravings and withdrawal symptoms. In addition, the methodology according to the invention also results in improved cognitive function.

It is yet another object of the present invention to provide a methodology and protocol for reducing patient dropout rates for those patients undergoing treatment for alcohol and/or psychostimulant addiction. The invention includes the administration of a compound that directly or indirectly selectively modulates chloride channel activity in a therapeutically effective quantity resulting in higher patient recovery rates compared to conventional treatments. This, in turn, results in lower patient dropout rates.

Optionally, it is another object of the present invention to provide for administration of therapeutically effective amounts of flumazenil in multiple doses at a predetermined rate which results in significantly lower patient dropout rates and fewer side effects in the patient.

BRIEF DESCRIPTION OF THE DRAWINGS

These and other features and advantages of the present invention will be appreciated, as they become better understood by reference to the following Detailed Description when considered in connection with the accompanying drawings, wherein:

FIG. 5 is a flowchart illustrating a first embodiment of an exemplary methodology to treat stimulant substance abuse; and FIG. 6 is a flowchart illustrating a second embodiment of an exemplary methodology to treat stimulant substance abuse.

DETAILED DESCRIPTION OF THE INVENTION

Figure 1:
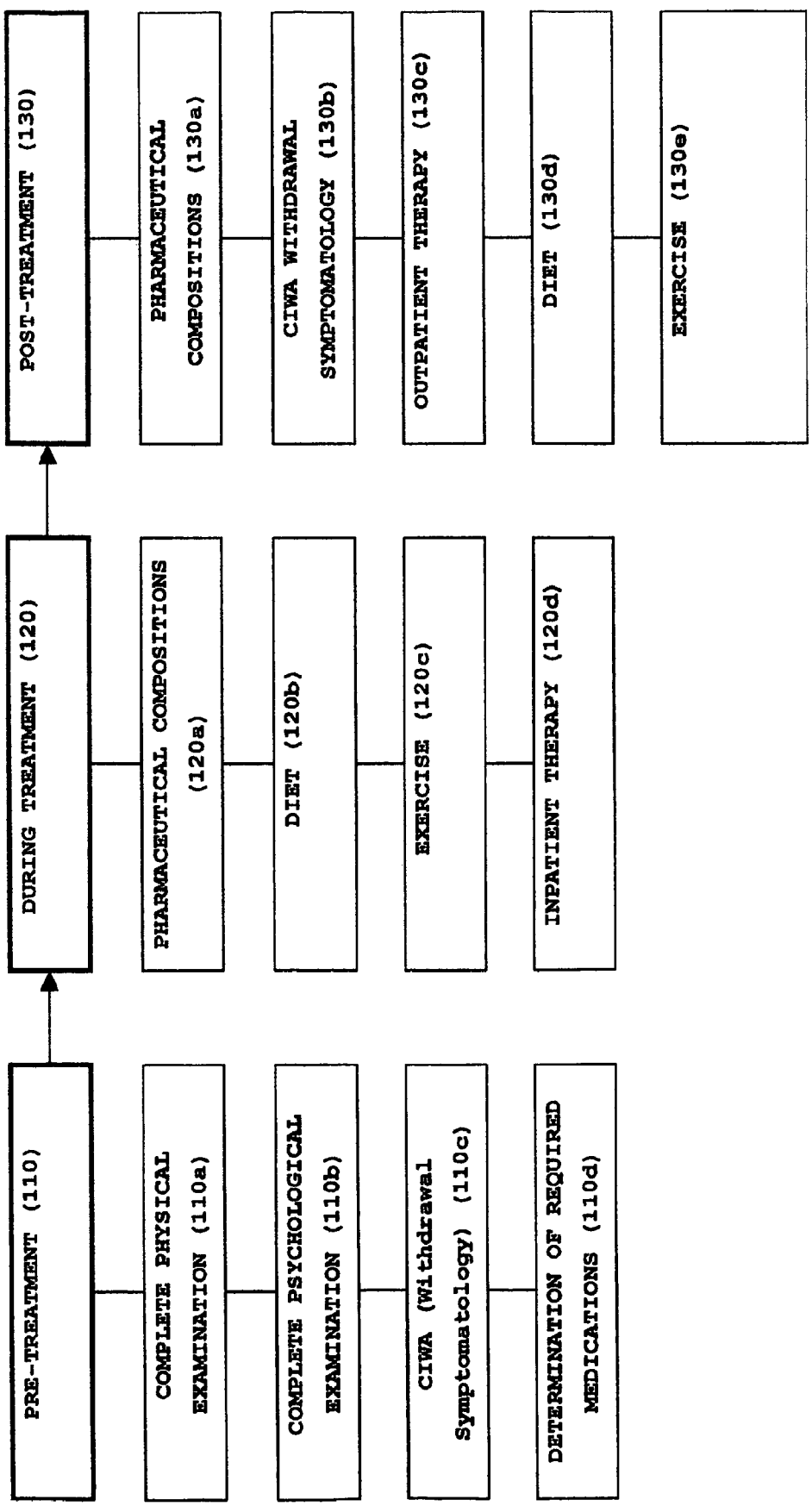
FIG. 1 is a flowchart depicting various pre-treatment, co-treatment, and post-treatment phases of an exemplary methodology for using pharmaceutical compositions from a class of compounds that directly or indirectly selectively modulate $GABA_A$ chloride channel activity to treat alcohol and/or psychostimulant substance abuse.

The present invention is directed towards methods and protocols for the treatment of alcohol and/or psychostimulant substance abuse based on safe and effective administration of a class of compounds that directly or indirectly selectively modulates chloride channel activity, such as, but not limited to flumazenil, and which requires a short period of time to effectively eradicate symptoms of alcohol and/or psychostimulant substance abuse.

The present invention provides for a comprehensive treatment approach for managing the recovery process for alcohol and/or stimulant substance abuse. The methodology of the present invention is also designed to reduce inpatient treatment time (2-3 days), improve treatment completion rates, reduce cravings, and decrease patient relapse rates versus current alcohol and/or stimulant abuse treatment options.

As used in this description, the term substance abuse is used to refer to the various physical and psychological states that manifest an individual's impaired control over alcohol and/or stimulant substance use, continued alcohol and/or stimulant substance use despite harm, compulsive alcohol and/or stimulant substance use, and/or cravings. The term is intended to include psychological dependence, physical dependence, tolerance, a maladaptive pattern of alcohol and/or stimulant substance use, preoccupation with alcohol and/or stimulant substance use, and/or the prevalence of withdrawal symptoms upon cessation of use.

As used in this description, the term drug is used to refer to prescription or non-prescription pharmaceutical compositions and/or medications that include an active ingredient and, optionally, non-active, buffering, or stabilizing ingredients, including pharmaceutically acceptable carriers or excipients suitable for the form of administration of said pharmaceutical compositions.

In particular, the term drug is used to refer to a class of compounds that directly or indirectly selectively modulates chloride channel activity ("Selective Chloride Channel Modulators"), e.g. chloride ion flow across the channel, with respect to $GABA_A$ receptors in the brain. One of ordinary skill in the art would appreciate that, as defined herein, the term Selective Chloride Channel Modulators is intended to cover the selective modulation of chloride channel activity and does not encompass full agonists of the $GABA_A$ receptor, such as benzodiazpenes.

In one embodiment, the Selective Chloride Channel Modulators comprises a partial allosteric modulator that acts with high affinity but low potency at $GABA_A$ receptor sites. The partial allosteric modulators of the present invention are capable of engaging a $GABA_A$ receptor site based upon a conformational compatibility with the $GABA_A$ receptor site. In one embodiment, the partial allosteric modulators of the present invention are capable of displacing, modifying, or otherwise limiting the affects of endogenous benzodiazepine inverse agonists by preventing their engagement with a $GABA_A$ receptor site. In another embodiment, the partial allosteric modulators of the present invention have a mild inverse agonist affect on the $GABA_A$ receptor due to a high affinity and low potency.

In another embodiment, the Selective Chloride Channel Modulators comprises a partial allosteric modulator that acts to reset $GABA_A$ receptivity and thereby increase receptivity and chloride channel ion flow without requiring alcohol.

In another embodiment, the Selective Chloride Channel Modulators comprise a composition that functions as a partial agonist of the $GABA_A$ receptor by displacing, modifying or otherwise limiting the affects of endogenous benzodiazepine inverse agonists, such as diazepam binding inhibitor (DBI), and that functions as an inverse agonist of the $GABA_A$ receptor if not in the presence of an endogenous benzodiazepine inverse agonist.

In another embodiment, Selective Chloride Channel Modulators comprise a composition that functions as a partial agonist of the $GABA_A$ receptor by displacing, modifying or otherwise limiting the affects of benzodiazepine inverse agonists, such as diazepam binding inhibitor (DBI), and that has substantially no affect on the $GABA_A$ receptor in the absence of a benzodiazepine inverse agonist.

In another embodiment, Selective Chloride Channel Modulators comprise certain imidazobenzodiazepines and derivatives of ethyl 8-fluoro-5,6-dihydro-5-methyl-6-oxo-4H-imidazo-[1,5-a][1,4]benzodiazepine-3-carboxylate, including various substitutions of in the carboxylate functional group, such as carboxylic acids, esters, acyl chlorides, acid anhydrides, amides, nitrites, alkyls, alkanes, cycloalkanes, alkenes, alcohols, aldehydes, ketones, benzenes, phenyls, and salts thereof. In another embodiment, Selective Chloride Channel Modulators comprise flumazenil and carboxylic acids, esters, acyl chlorides, acid anhydrides, amides, nitrites, alkyls, alkanes, cycloalkanes, alkenes, alcohols, aldehydes, ketones, benzenes, phenyls, and salts thereof.

As used in this description, the term patient refers to a male or female human being of any race, national origin, age, physiological make-up, genetic make-up, disease predisposition, height, or weight, and having any disease state, symptom or illness.

It should be appreciated that the administration of a Selective Chloride Channel Modulator may be achieved through any appropriate route of administration, for example, orally, inhaled, rectally, sublingually, bucally, transdermally, nasally, or parenterally, for which it will be formulated using the appropriate excipients for the form of administration. In one embodiment, the Selective Chloride Channel Modulator is administered intravenously (IV). In another embodiment, the Selective Chloride Channel Modulator is administered using an infusion pump. In another embodiment, the Selective Chloride Channel Modulator is administered using a syringe pump that provides the continuous, or physician-controlled, delivery of the drug. In another embodiment, the Selective Chloride Channel Modulator is administered from pre-filled syringes that automatically deliver a predetermined dose over an infusion period.

It should further be appreciated that the methods and processes of the present invention can be implemented in a computer system having a data repository to receive and store patient data, a memory to store the protocol steps that comprise the methods and processes of the present invention, a processor to evaluate patient data in relation to said protocol steps, a network interface to communicate via a network with other computing devices and a display to deliver information to users. In one embodiment, specific protocol steps are stored in said memory and compared against patient data to determine which protocol steps should be applied in accordance with the patient data. Results of the comparison are communicated to a user via a network and other computing devices or display. The methodologies of the present invention are therefore accessed, tailored, and communicated as a software program operating on any hardware platform.

Reference will now be made in detail to specific embodiments of the invention. While the invention will be described in conjunction with specific embodiments, it is not intended to limit the invention to one embodiment.

1. Introduction to an Exemplary Methodology

Referring to FIG. 1, the treatment methodology of the present invention 100 is a system consisting of multiple components administered on a pre-admittance, inpatient, outpatient, and post-discharge basis for the treatment of alcohol dependence. The methodology is designed to reduce cravings associated with and following alcohol withdrawal, and to help the dependent patient maintain abstinence and reduce harmful behavior during outpatient and follow-up care. The methodology will largely be described with reference to the alcohol dependence methodology in this section, but is not limited to such methodology. A separate methodology may be administered for psychostimulant, or combined alcohol and psychostimulant, dependence. Additionally, separate methodologies may be catered to outpatient vs. inpatient treatment settings.

As shown in FIG. 1, the treatment methodology 100 for alcohol dependence has multiple phases and components that, in combination, provide a comprehensive and integrated neurological, physiological, and psychosocial approach for the alcohol-dependent patient. Each component has been selected to address specific effects of chronic alcohol consumption and the corresponding symptoms of alcohol withdrawal, with the objective of restoring a balance in neurological circuits. The methodology does not address the specific physical injury, such as liver damage, that is often associated with alcohol dependence. It is, therefore, essential that each patient be assessed and the appropriate treatments be instituted to address physical injury, with due consideration for the potential interaction of any drugs used for this treatment with those used for the dependency treatment.

While the present methodology can be applied to any patient, it is preferred that the patient be equal to or greater than eighteen years old. It is also preferred that the patient meet at least a portion of the DSM IV criteria for substance dependence on stimulants or alcohol. The DSM IV criteria is known to those of ordinary skill in the art and can be described as a maladaptive pattern of alcohol and/or stimulant substance use, leading to clinically significant impairment or distress, as manifested by any of the following, occurring at any time in the same 12-month period:

(1) Tolerance, as defined by either of the following:
  a. A need for markedly increased amounts of the substance to achieve intoxication or desired effect.
  b. Markedly diminished effect with continued use of the same amount of the substance.
(2) Withdrawal, as manifested by either of the following:
  a. The characteristic withdrawal syndrome for the substance.
  b. The same (or a closely related) substance is taken to relieve or avoid withdrawal symptoms.
(3) The substance is often taken in larger amounts or over a longer period than was intended (loss of control).
(4) There is a persistent desire or unsuccessful efforts to cut down or control substance use (loss of control).
(5) A great deal of time is spent in activities necessary to obtain the substance, use the substance, or recover from its effects (preoccupation).
(6) Important social, occupational, or recreational activities are given up or reduced because of substance use (continuation despite adverse consequences).
(7) The substance use is continued despite knowledge of having a persistent or recurrent physical or psychological problem that is likely to have been caused or exacerbated by the substance (adverse consequences).

It should further be noted that certain exclusion criteria should be applied to the screening of patients. The exclusion criteria may be tailored to an outpatient or inpatient treatment scenario. For example, it is preferred not to treat a patient on an inpatient basis for alcohol or stimulant dependence where the patient has current medical or psychiatric problems that, per the screening physician, require immediate professional evaluation and treatment, has current medical or psychiatric problems that, per the screening physician, render the client unable to work successfully with the methodology or with the staff administering the treatment, has current benzodiazepine and other sedative-hypnotic-anxiolytic use (urine toxicology must be negative) or is taking anti-psychotic medication(s).

Similarly, it is preferred not to treat a patient on an inpatient basis for alcohol dependence where the patient has current medical or psychiatric problems that, per the screening physician, require immediate professional evaluation and treatment, has current medical or psychiatric problems that, per the screening physician, render the client unable to work successfully with the methodology or is currently taking tricyclic anti-depressants or benzodiazepines.

Patients admitted for the methodology for alcohol (and/or psychostimulant) dependence are initially treated with medications for 2 days of neurostabilization (which may include detoxification) along with nutritional supplements to ensure their supply does not limit the body's ability to restore an appropriate metabolic balance (such as physiological amino acid and protein turnover). Subsequent patient management includes maintenance pharmacotherapy with protocol components, combined with optional (but recommended) psychosocial and/or behavioral therapies, which are described in detail below. The combined effects of pharmacotherapy and psychosocial support are designed to minimize withdrawal symptoms, help prevent relapse, and reduce cravings for the dependent substance. Ongoing psychosocial and/or behavioral treatment is tailored to optimize the probability of long-term recovery.

2. Exemplary Methodology Components (100)

Referring back to FIG. 1, the exemplary treatment methodology 100 of the present invention comprises pre-treatment, co-treatment, and post-treatment phases further comprising various components of an exemplary methodology for using pharmaceutical compositions from a class of compounds that directly or indirectly selectively modulate $GABA_A$ chloride channel activity to treat addiction to alcohol and/or psychostimulants. As described herein, reference will be made to specific components of the individual phases of the treatment methodology 100. It should be noted, however, that the individual components comprising each phase of the methodology—pre-treatment, co-treatment, and post-treatment—may be performed in different orders and should be determined on a per-patient basis. Thus, any reference to administering the individual components of the phases of methodology 100 in a particular order is exemplary and it should be understood to one of ordinary skill in the art that the administration of methodology 100 may vary depending on the assessed needs of the patient.

a. Pre-Treatment (110)

Referring back to FIG. 1, prior to admittance into the treatment program of the present invention, each patient should undergo a pre-treatment analysis 110. The pre-treatment analysis 110 may be used to determine whether a patient is an optimal candidate for the treatment methodology of the present invention. In addition, the pre-treatment process 110 may be administered to prepare a patient for admittance into the treatment methodology 100 of the present invention. The pre-treatment phase typically includes, but is not limited to a complete physical examination 110a, a complete psychological examination 110b, a CIWA Assessment 110c, and a determination of required medications 110d. The components of the pre-treatment phase of the methodology 100 of the present invention are described in greater detail below.

i. Complete Physical Examination (110a)

Before starting the treatment, it is preferred that patient undergo a complete medical examination. The patient is preferably monitored to obtain a complete blood count, a biochemical profile [for example, creatinine, glucose, blood urea nitrogen (BUN), cholesterol (HDL and LDL), triglycerides, alkaline phosphatase, LDH (lactic dehydrogenase) and total proteins], hepatic function tests [GOT, GPT, GGT, bilirubin], electrocardiogram and, if need be, pregnancy test and x-ray examination. Exclusion criteria is applied to ensure no other acute or uncompensated illness exists within the patient and to ensure that the patient does not require, or is currently not taking, a drug that is contraindicated with flumazenil or another Selective Chloride Channel Modulator if being used.

ii. Complete Psychological Examination (110b)

Before starting the treatment, it is also preferred that patient undergo a complete psychological medical examination.

iii. Withdrawal Symptomatology (110c)

Before and after the administration of the Selective Chloride Channel Modulator, the withdrawal symptomatology should be measured using the CIWA-A evaluation (Adinoff et al., Medical Toxicology 3:172-196 (1988)), as well as heart rate and blood pressure.

iv. Determination of Required Medications (110d)

The physician in charge should make a determination, prior to treatment, if a patient diagnosed with any symptom or disorder, other than alcohol or psychostimulant addiction, should receive medication for this disorder. For example, a patient diagnosed with arterial hypertension should be prescribed with the appropriate medication or continue with any existing medication.

b. During Treatment (120)

Referring back to FIG. 1, if a patient is admitted into the treatment program of the present invention, the patient will then begin the during treatment phase 120 of the treatment methodology 100 of the present invention. During treatment, a patient will preferably be administered pharmaceutical compositions 120a, adhere to a prescribed diet 120b, maintain an exercise regimen 120c, and attend inpatient therapy sessions 120d. The exemplary components of the during treatment phase of the treatment methodology 100 are described in greater detail below, but are not limited to such options.

i. Pharmaceutical Compositions (120a)

Various pharmaceutical compounds may be administered during treatment with a benzodiazepine antagonist as with the methodology of the present invention. These are listed below.

1. Selective Chloride Channel Modulator

In one embodiment, the Selective Chloride Channel Modulator flumazenil is used because it functions to effectively regulate $GABA_A$ receptor activity and minimize the severity of conventional withdrawal symptoms. The use of flumazenil may normalize shifts in neuronal $GABA_A$ activity and subsequent dopamine malfunctions resulting from chronic exposure to ethanol. Specifically, when used in accordance with the novel invention presented herein, flumazenil is anxiolytic, thereby ameliorating an important withdrawal symptom, and decreases cravings.

2. Gabapentin a. Use of Gabapentin

Gabapentin is an anxiolytic and anticonvulsant medication typically prescribed to patients suffering from epilepsy (effectively lowers brain glutamate concentrations) and has also been used in the treatment of anxiety disorders such as social anxiety disorder and obsessive-compulsive disorder. Gabapentin compliments flumazenil in helping normalize GABA and glutamate transmission, thus enhancing GABA tone.

Gabapentin was originally designed as a structural analog of GABA. It likely operates as a calcium N-channel blocker. Gabapentin also exhibits post-synaptic effects modulating NMDA-mediated transmission by 1) reducing NMDA/Glutamatergic tone and 2) indirectly helping compensate for reduced GABAergic tone due to upregulated NMDA activity in the withdrawn state. Gabapentin provides for an improved quality and quantity of sleep and an improved anxiety state. As a result of its above-mentioned qualities, gabapentin decreases withdrawal symptoms.

b. Key Pharmacologic Safety Considerations for the Use of Gabapentin

Prior to administering gabapentin to a patient, it is essential to assess the patient for interactions and contraindications. Gabapentin is to be used in adjunctive therapy in the treatment of epilepsy seizures (partial) and for the management of postherpetic neuralgia. Gabapentin is not appreciably metabolized and is excreted unchanged with an elimination half-life of 5-7 hours. Possible side effects from the use of gabapentin are dizziness, somnolence, other symptoms/signs of CNS depression, nausea, ataxia, tremor, and peripheral edema. In persons with epilepsy, abrupt discontinuation may increase seizure frequency. No clinically significant drug interactions have been reported in the literature.

3. Hydroxyzine HCl

Hydroxyzine, an H1 histamine receptor antagonist, is indicated for treatment of generalized anxiety disorder and for use in the management of withdrawal from substance dependence during both the initial phase of inpatient treatment and post-discharge care (as necessary). It also has anti-emetic and skeletal muscle relaxation benefits and can be used as a sedative. This sedative effect can be useful for treating the sleep-disordered breathing and increased periodic leg movements that contribute to the insomnia often seen in patients recovering from alcohol dependency. This helps address on-going insomnia that, for some patients, is significantly associated with subsequent alcoholic relapse.

Hydroxyzine is rapidly absorbed and yields effects within 15-30 minutes after oral administration. In addition, hydroxyzine aids the substance withdrawal process through anxiolytic, anti-nausea, relaxant, and various other properties. It should be noted that the effects of other sedating or tranquilizing agents might be synergistically enhanced with the administration of hydroxyzine. Exemplary drugs include pharmacological compositions having the trade names Atarax and Vistaril.

4. Vitamin B a. Fortified Vitamin B Complex

Chronic alcohol consumption depletes the levels of several vitamins, particularly the B vitamins (also known as the stress vitamins). These vitamins are required by the body to convert food into energy, maintain the integrity of tissues such as the skin and liver, and combat physical or emotional stress. Administration of vitamin B complex as part of the management of the alcohol-dependent patient may help to ameliorate the risk of Wernicke-Korsakoff syndrome and alcoholism-induced cognitive deficit. The present invention preferably includes the provision of a nutritional supplement of fortified vitamin B-complex (thiamine—B1, riboflavin—B2, niacin—B3, pyridoxine—B6, folic acid—B9, cyanocobalamin—B12, pantothenic acid, and biotin) to patients daily during stabilization with the methodology and post-discharge for as long as medically beneficial.

b. IV Vitamin B Supplement

Alcohol abusers tend to have poor nutritional status, exacerbated by poor diet, gastritis, duodenitis, frequent vomiting, physical illness, and weight loss. Thus, there is a need for parenteral vitamins. Thiamine absorption from oral treatment tends to vary; alcohol in the gut interferes with absorption. Thus, there is a potentially large thiamine deficiency in alcohol dependence. Oral dosing is unlikely to meet maintenance requirements. Thiamine decreases sodium transport in alcohol dependence. In addition, it is a catalyzer of key metabolic actions of GABA.

5. Protein Supplement Drink

Chronic alcohol consumption increases the body's overall rate of metabolism, and alcohol-dependent subjects often have reduced skeletal muscle synthesis and skeletal muscle mass. Alcohol reduces protein synthesis in a range of tissues, including but not limited to skeletal muscle. This can lead to a net loss of protein from and impaired function in important organs and tissues such as the heart, liver and kidneys. To counteract these effects, a protein supplement drink is preferably provided daily to the patient during inpatient stabilization with the methodology. In addition, the increased levels of serum amino acids (such tyrosine and tryptophan) provide the substrate to help re-establish alcohol- and withdrawal-induced alterations in levels of neurotransmitters such as dopamine and serotonin.

6. Glutamine

Glutamine is the most abundant amino acid in the body and is an essential nutrient for actively replicating cells, such as those of the immune system. Glutamine is also a precursor for both glutamate and GABA. In skeletal muscle glutamine is the most abundant amino acid and its depletion is associated with loss of muscle mass, a process that can be reversed by glutamine supplementation.

Alcohol has direct effects on the innate immune system. Alcohol predisposes dependent patients to infections and sepsis by blunting the initial response to pathogens. Withdrawing alcohol does not immediately reverse this effect. Glutamine, given as a nutritional supplement, is an important part of the methodology. Glutamine supplementation provides an immediate supply of fuel to the immune system, possibly enhancing immune function. Glutamine supplementation helps to restore the plasma and muscle levels of glutamine, which may help reverse the loss of protein typically seen in alcohol-dependent patients.

ii. Diet (120b)

Depending upon the results of the initial examination, a universal or patient-specific diet plan may optionally be administered in conjunction with the methodology.

iii. Exercise (120c)

Depending upon the results of the initial examination, a universal or patient-specific exercise programs may optionally be administered in conjunction with the methodology.

iv. Inpatient Therapy (120d)

A structured program for cognitive behavior therapy is preferably implemented in the methodology. Individual psychotherapy is focused on a plurality of interventions, such as cognitive restructuring, work therapy, prevention of relapse, and stress reduction aimed at rehabilitating the social, family, work, personal and leisure life of the patient.

c. Post-Treatment (130)

Referring back to FIG. 1, after a patient successfully completes the during treatment phase of the methodology of the present invention 100, each patient will be prescribed a post-treatment regimen 130 to follow, which includes, but is not limited to, the administration of pharmaceutical compositions 130a, a CIWA assessment 130b, outpatient therapy 130c, a diet program 130d, and an exercise regimen 130e. The components of the post-treatment phase of the methodology of the present invention 100 are described in greater detail below.

i. Pharmaceutical Compositions (130a)

Before discharge from the hospital, one or more of the following compositions or drugs are prescribed. Preferably, the compositions or drugs can be administered in oral form to enable greater patient compliance and convenience. It should be appreciated that, to the extent any of drugs described herein are not available in the jurisdiction in which this invention is being practiced, equivalent functioning drugs may be used.

1. Vitamin B a. Fortified Vitamin B Complex

Chronic alcohol consumption depletes the levels of several vitamins, particularly the B vitamins (also known as the stress vitamins). These vitamins are required by the body to convert food into energy, maintain the integrity of tissues such as the skin and liver, and combat physical or emotional stress. Administration of vitamin B complex as part of the management of the alcohol-dependent patient may help to ameliorate the risk of Wernicke-Korsakoff syndrome and alcoholism-induced cognitive deficit. The present invention preferably includes the provision of a nutritional supplement of fortified vitamin B-complex (thiamine—B1, riboflavin—B2, niacin—B3, pyridoxine—B6, folic acid—B9, cyanocobalamin—B12, pantothenic acid, and biotin) to patients daily during stabilization with the methodology and post-discharge for as long as medically beneficial.

b. IV Vitamin B Supplement

Alcohol abusers tend to have poor nutritional status, exacerbated by poor diet, gastritis, duodenitis, frequent vomiting, physical illness, and weight loss. Thus, there is a need for parenteral vitamins. Thiamine absorption from oral treatment tends to vary; alcohol in the gut interferes with absorption. Thus, there is a potentially large thiamine deficiency in alcohol dependence. Oral dosing is unlikely to meet maintenance requirements. Thiamine decreases sodium transport in alcohol dependence. In addition, it is a catalyzer of key metabolic actions of GABA.

2. Piracetam

Piracetam is a CNS (central nervous system) stimulant with no known toxicity or addictive properties. Piracetam is used as a supplement to improve cognitive functioning in patients suffering from alcohol withdrawal. Piracetam is preferably prescribed in the following dosages for this methodology: 3 grams every morning for one week, followed by 800 mg twice daily for one month.

3. Fluoxetine

Fluoxetine hydrochloride is an antidepressant for oral administration; it is chemically unrelated to tricyclic, tetracyclic, or other available antidepressant agents. It is designated (±)-N-methyl-3-phenyl-3-[(a,a,a-trifluoro-p-tolyl)-oxy]propylamine hydrochloride. As part of this methodology, it is used to treat symptoms of anxiety and depression associated with alcohol and/or psychostimulant dependence. The suggested dosage is 10 to 20 mg of fluoxetine every morning for two months, but may be increased or decreased on a per patient basis.

4. Clomethiazole

The suggested dosage of clomethiazole (or chlormethiazole) is about 200 mg, and more specifically about 192 mg, in both the morning and evening for 1 week and eliminated during the second week.

5. Disulfuram

Disulfuram, an inhibitor of aldehyde dehydrogenase in the liver, increases blood acetaldehyde concentrations and subsequently induces symptoms of acetaldehyde syndrome, including (but not limited to) vomiting, weakness, confusion, vasodilation in the head, and throbbing headache. This agent is used in the methodology for six months post-discharge to induce averse associations with alcohol consumption, thus helping to sustain the recovery process. In one embodiment, the dosage is 250 mg every morning as long as medically beneficial.

6. Gabapentin a. Use of Gabapentin

Gabapentin is an anxiolytic and anticonvulsant medication typically prescribed to patients suffering from epilepsy (effectively lowers brain glutamate concentrations) and can be used in the treatment of anxiety disorders such as social anxiety disorder and obsessive-compulsive disorder. Gabapentin compliments flumazenil in helping normalize GABA and glutamate transmission, thus enhancing GABA tone.

Gabapentin was originally designed as a structural analog of GABA. It likely operates as a calcium N-channel blocker. Gabapentin also exhibits post-synaptic effects modulating NMDA-mediated transmission by 1) reducing NMDA/Glutamatergic tone and 2) indirectly helping compensate for reduced GABAergic tone due to upregulated NMDA activity in the withdrawn state. Gabapentin can provide for an improved quality and quantity of sleep and an improved anxiety state. As a result of its above-mentioned qualities, gabapentin decreases withdrawal symptoms.

b. Key Pharmacologic Safety Considerations for the Use of Gabapentin

Prior to administering gabapentin to a patient, it is essential to assess the patient for interactions and contraindications. Gabapentin is to be used in adjunctive therapy in the treatment of epilepsy seizures (partial) and for the management of postherpetic neuralgia. Gabapentin is not appreciably metabolized and is excreted unchanged with an elimination half-life of 5-7 hours. Possible side effects from the use of gabapentin are dizziness, somnolence, other symptoms/signs of CNS depression, nausea, ataxia, tremor, and peripheral edema. In persons with epilepsy, abrupt discontinuation may increase seizure frequency. No clinically significant drug interactions have been reported in the literature.

7. Other Drugs

Optionally, after the final Selective Chloride Channel Modulator administration, non-stimulant drugs can be administered. Specifically, after the final flumazenil treatment, non-benzodiazepine, barbiturate drugs or drugs with a direct chloride channel effect can be administered.

ii. Withdrawal Symptomatology (130b)

Before and after the administration of flumazenil, the withdrawal symptomatology should be measured using the CIWA-A evaluation (Adinoff et al., Medical Toxicology 3:172-196 (1988)), as well as heart rate and blood pressure.

iii. Outpatient Therapy (130c)

Psychotherapy/behavioral therapy and counseling may be critical for the success of alcohol and/or stimulant substance-dependency treatment when adopting a pharmacological approach. Thus, the methodology also provides for a maintenance program that includes medications and incentives for the patient to continue with their recovery process through continuing care programs. The methodology is not considered a replacement for behavioral therapy and is not a cure. Due to the complexity of alcohol and/or stimulant substance dependence, patients benefit most from a combination of pharmacologic and behavioral interventions.

As part of the treatment program, patients are preferably instructed to attend the outpatient treatment center for 9 months with decreasing frequency [once a week for the first three months, once every two weeks during the second three months, and once a month during the third three months].

Likewise, a semi-structured follow-up of cognitive behavior therapy is preferably implemented. Individual and family psychotherapy is focused on a plurality of interventions, including cognitive restructuring, work therapy, prevention of relapse, and stress reduction, aimed at rehabilitating the social, family, work, personal and leisure life of the patient.

iv. Diet (130d)

Depending upon the results of the initial examination, a universal or patient-specific diet plan may optionally be administered in conjunction with the methodology.

v. Exercise (130e)

Depending upon the results of the initial examination, a universal or patient-specific exercise programs may optionally be administered in conjunction with the methodology.

3. Methodology Embodiments

Reference will now be made in detail to specific embodiments and examples of the methods and protocols of the present invention. While the invention will be described in conjunction with specific embodiments, it is not intended to limit the invention to one embodiment. In addition, many combinations of the methodology components described above are possible; thus, the invention is not limited to such examples as provided.

In one specific embodiment, the present invention relates to the use of a therapeutically effective quantity of a drug, namely a Selective Chloride Channel Modulator, such as, but not limited to, flumazenil, in a methodology for treatment of alcohol and/or psychostimulant dependency. More specifically, the invention relates to the use of flumazenil in multiple doses for a predetermined time period as part of the treatment methodology. When administered in accordance with the present invention, a therapeutically effective amount of the drug is maintained in the patient, thereby significantly reducing cravings for alcohol. The methodology of the present invention also provides for the administration of flumazenil without significant side effects.

Thus, in one embodiment, a method is provided for the treatment of alcohol and/or psychostimulant abuse that includes the administration to a patient in need of said treatment of a therapeutically effective quantity of flumazenil between 0.5 mg/day and 10 mg/day, specifically between 1.0 and 3.0 mg/day, and even more specifically between 1.5 and 2.5 mg/day, broken down into multiple doses of flumazenil between 0.2 and 0.3 mg and intended for administration during predetermined time periods or intervals, until said therapeutically effective quantity of flumazenil to treat alcohol and/or psychostimulant dependency has been reached. In one embodiment, the predetermined time period is in the range of 1 and 15 minutes and the "per dose" quantity of flumazenil is between 0.1 and 0.3 mg.

One of ordinary skill in the art would appreciate that the individual doses can range in amount, and the time interval between the individual doses can range in amount, provided that the total dose delivered is in the range of 0.5 mg/day and 10.0 mg/day and the individual doses are delivered at relatively consistent time intervals. Therefore, the time period intervals can range from 1, 2, 3, 4, 5, 6, 7, 8, 9, 10, 11, 12, 13, 14, 15, 16, 17, 18, 19, 20, 21, 22, 23, 24, or 25 minutes or fractions thereof. Doses delivered at each time period, separated by the time intervals, can be between 0.1 and 0.3 mg, or fractions thereof, keeping in mind the total drug delivered is preferably less than 10.0 mg/day. The present invention therefore provides for the delivery of multiple, sequential doses, delivered at substantially consistent time intervals.

Conventional uses of flumazenil comprise either singular doses or much larger doses over shorter periods of time and are directed toward addressing anesthesia, conscious sedation, or benzodiazepine overdose. Further, Romazicon, a brand name for flumazenil as marketed and sold by Roche, is expressly indicated to complicate the management of withdrawal syndromes for alcohol, barbiturates and cross-tolerant sedatives and was shown to have an adverse effect on the nervous system, causing increased agitation and anxiety. For a single dose to address anesthesia and conscious sedation, it is conventionally recommended to use a dose of 0.2 mg to 1 mg of Romazicon with a subsequent dose in no less than 20 minutes. For repeat treatment, 1 mg doses may be delivered over five minutes up to 3 mg doses over 15 minutes. In benzodiazepine overdose situations, a larger dose may be administered over short periods of time, such as 3 mg doses administered within 6 minutes. One of ordinary skill in the art would appreciate that, relative to the present invention, this dosing regimen either fails to maintain a presence of flumazenil in the bloodstream for extended periods of time (over a 12 to 24 hour period) or presents excessive amounts of flumazenil at any given time. Moreover, such conventional uses of flumazenil are not directed toward the treatment of alcohol or stimulant dependence.

In the treatment methodology of the present invention, flumazenil can be safely administered to patients in small quantities, applied in multiple doses during predetermined time periods/intervals, until a therapeutically effective quantity of flumazenil to treat alcohol and/or psychostimulant dependency has been reached. Thus, it is possible to administer flumazenil in smaller doses to obtain the desired therapeutic response, reducing the risk of secondary effects in the patient (as a result of reducing the quantity of drug administered per dose applied).

In addition, the administration method of the present invention provides a better use of flumazenil to treat the symptoms of alcohol and/or psychostimulant withdrawal and to reduce the unnecessary consumption of said drug, thereby increasing convenience and the quality of life of the patient and reducing cost, to treat alcohol and/or psychostimulant dependency in a very short period of time.

The method for the treatment of alcohol dependency provided by this invention is applicable to any patient who, when the treatment is to begin, has no acute or uncompensated illness, or is not taking medication contraindicated with the Selective Chloride Channel Modulator, such as flumazenil. In general, the method of treatment of alcohol and/or psychostimulant dependency provided by this invention begins with a complete medical and psychological examination, as described in detail above. Before and after administration of flumazenil, the symptoms of alcohol withdrawal, heart rate, and blood pressure are evaluated. If the patient presents with mild to moderate anxiety, it is possible to administer an appropriate therapeutic agent, for example, clomethiazole, before administration of flumazenil, as described above.

Once inpatient treatment has concluded, as part of the therapeutic program, the patient must continue pharmacological treatment and continue sessions with his therapist to evaluate his progress. The treatment is supplemented by a semi-structured therapy regime to monitor the cognitive behavior of the patient. According to another embodiment, alcohol dependent patients may be treated on an outpatient basis for 48 hours.

While references above have been made to inpatient treatment, it should be appreciated that an outpatient treatment regimen is possible, provided that the patient criteria is met, as previously described. It should further be appreciated that in both outpatient and inpatient treatment methodologies, Clinical Inventory Withdrawal Assessments (CIWA-Ar) should be utilized for assessment of withdrawal.

For example, for inpatient alcohol dependency treatment, the following CIWA evaluation guide can be used:

TABLE 1

Inpatient Alcohol CIWA-Ar Evaluation Guide

| | | |
|---|---|---|
| Pre-admission Screening | CIWA-Ar | Transfer to appropriate medical facility for detoxification if score is ≧15, and/or if acute medical or psychiatric problems are present. |
| Day 1 (a.m. of potential admission) | CIWA-Ar | Transfer to appropriate medical facility for detoxification if score is ≧15, and/or if acute medical or psychiatric problems are present. |
| Day 1 Pre-infusion | CIWA-Ar | Track CIWA-Ar scores to determine direction and potential acceleration of scores. |
| Day 1 Post-infusion | CIWA-Ar | Track CIWA-Ar scores to determine direction and potential acceleration of scores. |
| Day 1 9pm[1.] | CIWA-Ar | Day 3 required if CIWA ≧10 |
| Day 2 Pre-infusion[1.] | CIWA-Ar | Day 3 required if CIWA ≧10 |
| Day 2 Post-infusion[1.] | CIWA-Ar | Day 3 required if CIWA >6. Also can serve as discharge evaluation. |

[1.]A patient meeting any one of these scores requires a 3$^{rd}$ treatment.

For outpatient alcohol dependency treatment, the following CIWA evaluation guide can be used:

TABLE 2

Outpatient Alcohol CIWA-Ar Evaluation Guide

| | | |
|---|---|---|
| Screening | CIWA-Ar | Recommend in-patient treatment if score is ≧6 but not greater than 15. Transfer to appropriate medical facility for detoxification if score is ≧15, and/or if acute medical or psychiatric problems are present. |
| Day 1 (a.m. of potential admission) | CIWA-Ar | Transfer to appropriate medical facility for detoxification if score is ≧15, and/or if acute medical or psychiatric problems are present. |
| Day 1 Post-infusion | CIWA-Ar | Daily discharge criteria requires a CIWA-Ar score of less than 6. |
| Day 2 Post-infusion | CIWA-Ar | Daily discharge criteria requires a CIWA-Ar score of less than 6. |

Figure 2:
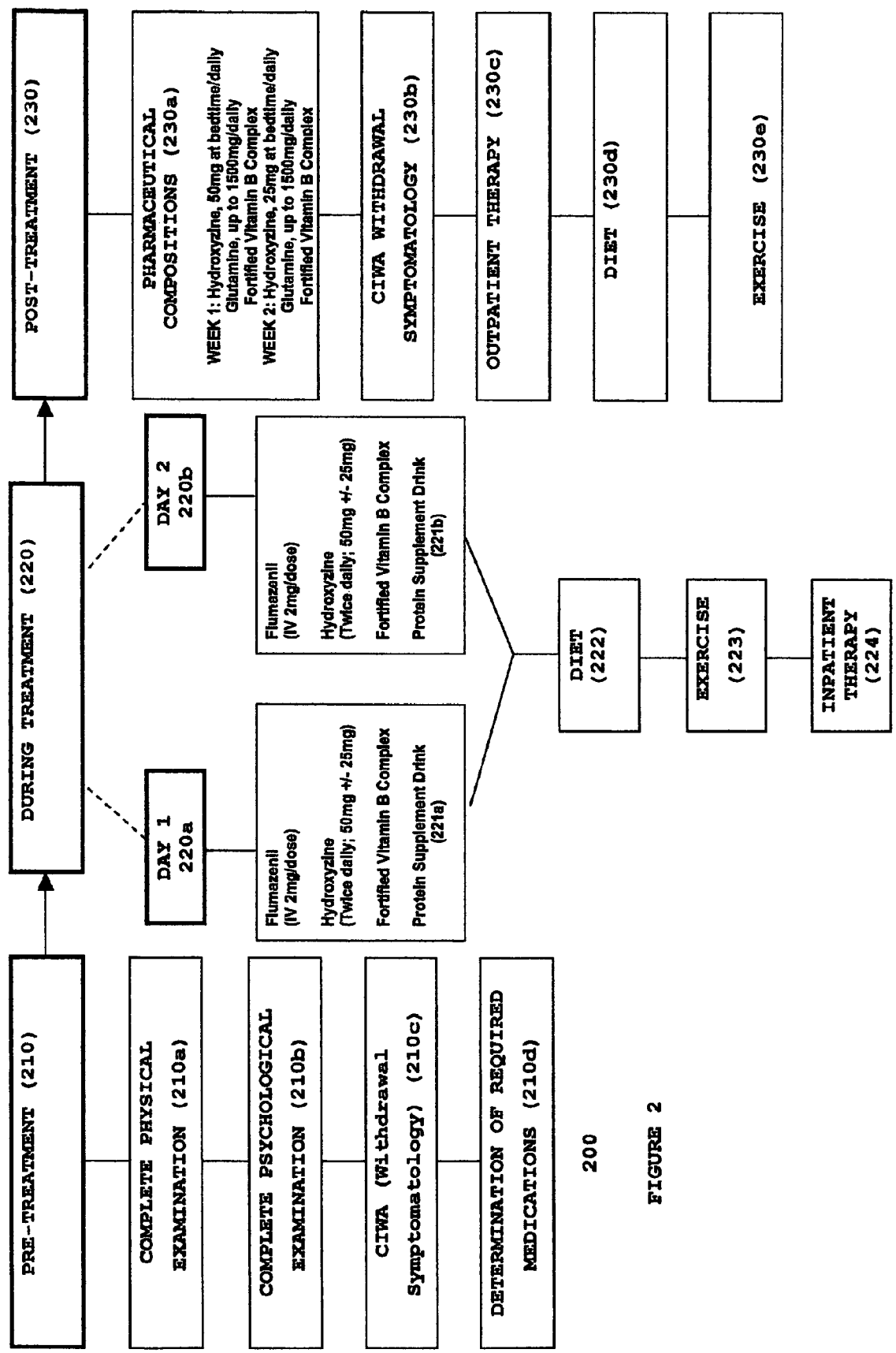
FIG. 2 is a flowchart illustrating a first embodiment of an exemplary methodology to treat alcohol substance abuse.

Now referring to FIG. 2, in a first exemplary methodology 200 for treating alcohol withdrawal, a patient undergoes the aforementioned pre-treatment regimen 210, which may include a complete physical examination 210a, a complete psychological examination 210b, a CIWA assessment 210c, and determination of required medications 210d.

On day 1 220a of treatment phase 220, the patient receives pharmaceutical compositions 221a, including flumazenil via an intravenous infusion, ultimately delivering a total amount of 2 mg per dosing interval. The patient further receives 50 mg of hydroxyzine twice daily plus or minus 25 mg as may be required. The patient further receives fortified vitamin B complex daily and a protein supplement drink daily in the morning.

On day 2 220b of treatment, the patient receives pharmaceutical compositions 221b, including flumazenil via an intravenous infusion, ultimately delivering a total amount of 2 mg per dosing interval. The patient further receives 50 mg of hydroxyzine twice daily plus or minus 25 mg as may be required. The patient further receives fortified vitamin B complex daily and a protein supplement drink daily in the morning.

Also during treatment, the patient may be prescribed a diet plan 222, exercise regiment 223, and inpatient therapy 224.

In the post-treatment phase 230 after discharge, for one week, the patient receives various pharmaceutical compositions 230a, including 50 mg of hydroxyzine at bedtime or for sleep and, for a subsequent week, the patient receives 25 mg of hydroxzine at bedtime or for sleep. For two weeks, the patient also receives glutamine titrated up to 1500 mg per day and fortified vitamin B complex daily. The patient may also receive additional post-treatment options, including a CIWA Assessment 230b, outpatient therapy 230c, and a diet and exercise regimen 230d, 230e.

Figure 3:
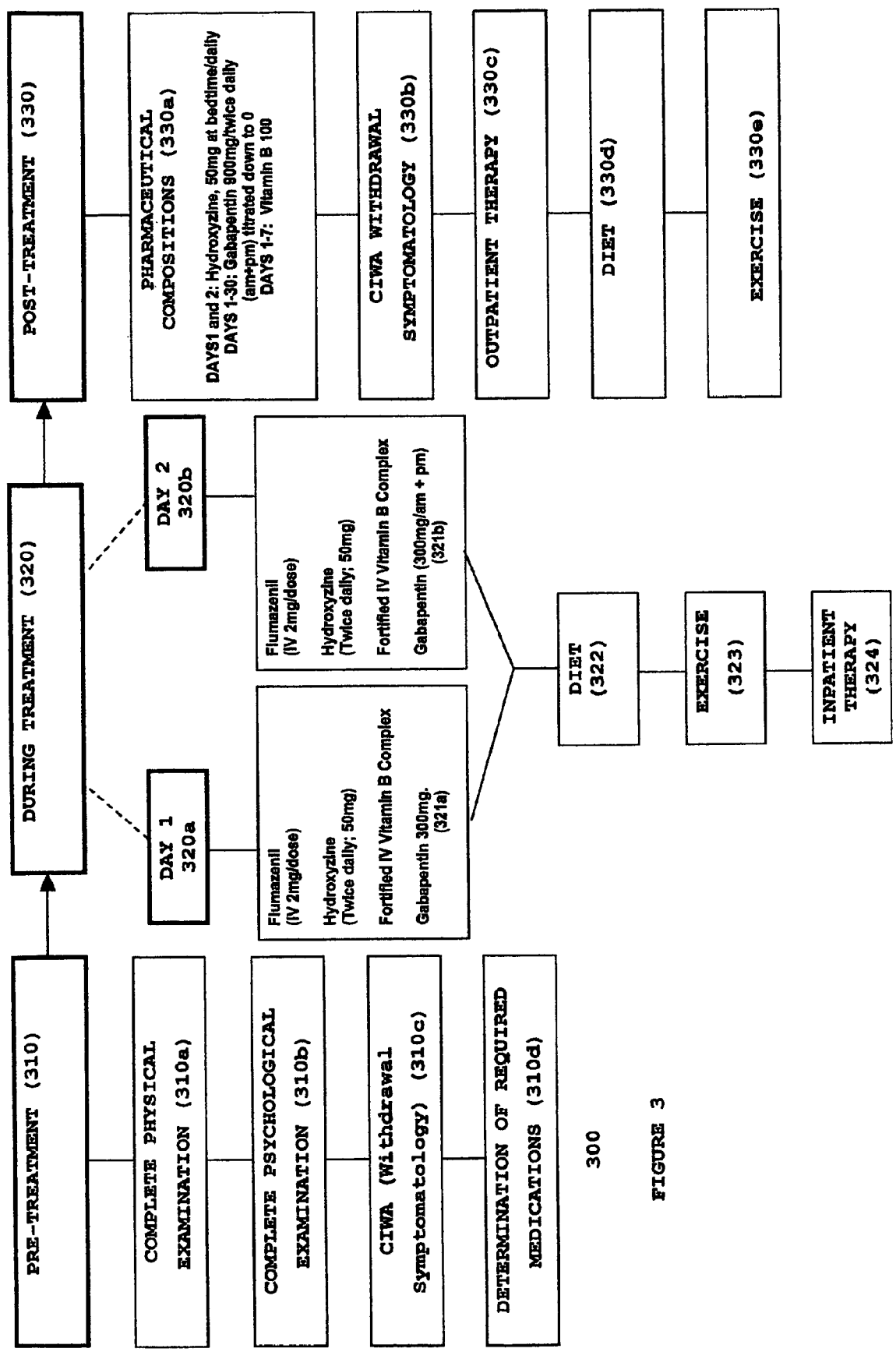
FIG. 3 is a flowchart illustrating a second embodiment of an exemplary methodology to treat alcohol substance abuse.

Referring now to FIG. 3, in a second exemplary methodology for treating alcohol withdrawal 300, a patient undergoes the aforementioned pre-treatment regimen 310, which may include a complete physical examination 310a, a complete psychological examination 310b, a CIWA assessment 310c, and a determination of required medications 310d.

On day 1 330a of treatment phase 330, the patient receives various pharmaceutical compositions 321a, including flumazenil via an intravenous infusion, ultimately delivering a total amount of 2 mg per dosing interval. The patient further receives 50 mg of hydroxyzine during the day and 50 mg of hydroxyzine at bedtime or in the evening. The patient further receives IV Vitamin B Complex and oral Gabapentin at a dose of 300 mg.

On day 2 330b of treatment phase 330, the patient receives various pharmaceutical compositions 321b, including flumazenil via an intravenous infusion, ultimately delivering a total amount of 2 mg per dosing interval. The patient further receives 50 mg of hydroxyzine during the day and 50 mg of hydroxyzine at bed or in the evening. The patient further receives IV Vitamin B Complex and oral Gabapentin at a dose of 300 mg in the afternoon and evening or at bedtime.

In addition, during treatment phase 320, a patient may be prescribed a diet plan 322, an exercise regimen 323, and inpatient therapy 324.

After discharge, for days one and two of post-treatment phase 330, the patient receives pharmaceutical compositions 330a, including 50 mg of hydroxyzine at bedtime or in the evening. For 30 days, the patient receives Gabapentin at a dose of 900 mg in the afternoon and evening or at bedtime then titrating down to 0. For one week, the patient also receives vitamin B 100 daily. The patient may also optionally receive a CIWA assessment 330b, outpatient therapy 330c, a diet plan 330d, and an exercise regiment 330e.

Figure 4:
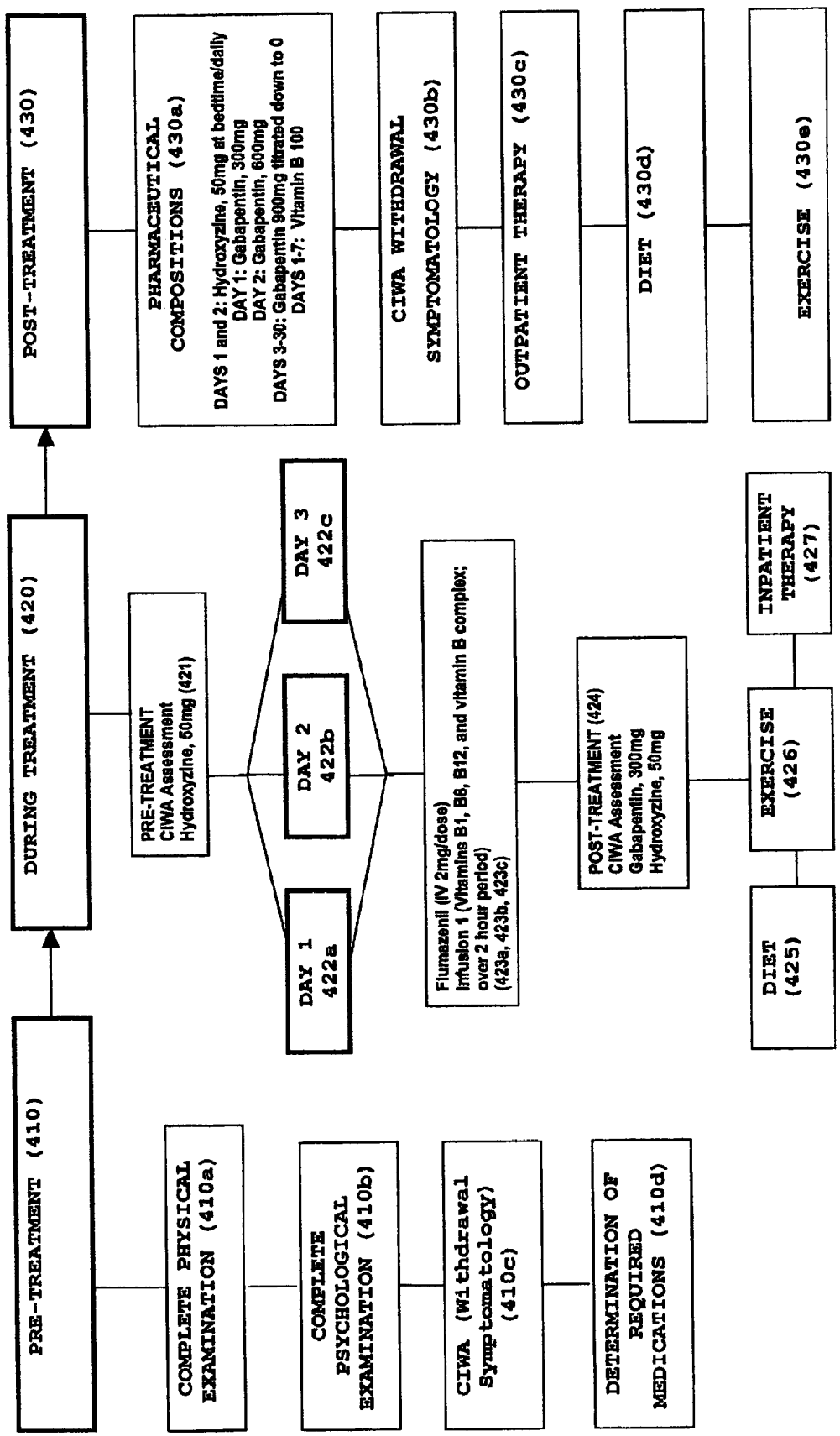
FIG. 4 is a flowchart illustrating a third embodiment of an exemplary methodology to treat alcohol substance abuse.

Referring now to FIG. 4, in a third exemplary methodology for treating alcohol withdrawal 400, a patient undergoes the aforementioned pre-treatment regimen 410, which may include a complete physical examination 410a, a complete psychological examination 410b, a CIWA assessment 410c, and a determination of required medications 410d.

During treatment phase 420, the patient undergoes a pre-treatment procedure 421 that includes a CIWA assessment and the administration of hydroxyzine at a dose of 50 mg. On day one 422a of treatment phase 420, a first infusion 423a is administered to the patient. The first infusion includes vitamin B1, vitamin B6, vitamin B12, and vitamin B complex and 2 mg of flumazenil over a period of 2 hours. After the first infusion, the patient undergoes a post-treatment procedure 424, typically in the late afternoon to evening that includes a CIWA assessment, the administration of Gabapentin at a dose of 300 mg, and the administration of hydroxyzine at a dose of 50 mg in the evening or bedtime.

On day two 422b of treatment phase 420, a patient undergoes a pre-treatment procedure 421 that includes a CIWA assessment and the administration of hydroxyzine at a dose of 50 mg. A second infusion 423b is then administered to the patient. The second infusion includes vitamin B1, vitamin B6, vitamin B12, and vitamin B complex and 2 mg of flumazenil over a period of 2 hours. After the second infusion, the patient undergoes a post-treatment procedure 424, typically in the late afternoon to evening that includes a CIWA assessment, the administration of Gabapentin at a dose of 300 mg, and the administration of hydroxyzine at a dose of 50 mg in the evening or bedtime.

During treatment phase 420 may also optionally include a diet plan 425, an exercise regimen 426, and inpatient therapy 427.

After discharge, the patient is monitored based on the CIWA assessment 430b and the patient's medical condition. Optionally, prior to discharge, the patient undergoes a third day 422c of treatment 420 that is similar to day 2 422b, if warranted by the patient's medical condition and/or CIWA assessment.

At discharge, in post-treatment phase 430, the patient is given pharmaceutical compositions 430a, which include 50 mg of hydroxyzine on days 1 and 2 at bedtime. The patient is also given gabapentin in the following amounts: 300 mg on day 1; 600 mg on day 2; and on days 3-30, 900 mg titrated down to zero. The patient is also given an Oral Vitamin B 100 complex daily for one week. Optionally, the patient may be prescribed outpatient therapy 430c, a diet plan 430d, and an exercise regimen 430e.

Referring now to FIG. 5, in a first exemplary methodology for treating stimulant withdrawal 500, a patient undergoes the aforementioned pre-treatment regimen 510. Pre-treatment regimen 510 may include a complete physical examination 510a, a complete psychological examination 510b, a CIWA assessment 510c, and a determination of required medications 510d.

On day 1 520a, day 2 520b and day 3 520c of treatment phase 520, the patient receives pharmaceutical compositions 521, including flumazenil via an intravenous infusion, ultimately delivering a total amount of 2 mg per dosing interval. The patient further receives 50 mg of hydroxyzine twice daily plus or minus 25 mg as may be required. The patient further receives fortified vitamin B complex daily and a protein supplement drink daily in the morning.

This treatment regimen 520, preferably day 1 520a and day 2 520b only, is repeated after three weeks 522. During both phases of the treatment phase 520, the patient may be prescribed a diet plan 523, an exercise regimen 524, and inpatient therapy 525.

In post-treatment phase 530, after discharge, the patient receives pharmaceutical compositions 530a, which include 50 mg of hydroxyzine at bedtime or for sleep for one week and, for a subsequent week, 25 mg of hydroxyzine at bedtime or for sleep. For two weeks, the patient also receives glutamine titrated up to 1500 mg per day and fortified vitamin B complex daily. The patient further receives Gabapentin titrated up to 1200 mg per day for six months. This regimen is interrupted for a second round of treatments 522, as described above, after three weeks have elapsed from the first round of treatments and restarted thereafter.

Now referring to FIG. 6, in a second exemplary methodology for treating stimulant withdrawal 600, a patient undergoes the aforementioned pre-treatment regimen 610. Pre-treatment regimen 610 may include a complete physical examination 610a, a complete psychological examination 610b, a CIWA assessment 610c, and a determination of required medications 610d.

On day 1 620a, day 2 620b and day 3 620c of treatment phase 620, the patient receives pharmaceutical compositions 621, including flumazenil via an intravenous infusion, ultimately delivering a total amount of 2 mg per dosing interval. The patient further receives 50 mg of hydroxyzine. The patient further receives fortified vitamin B complex daily and Gabapentin at a dose of 300 mg.

This treatment regimen 620, preferably day 1 620a and day 2 620b only, is repeated after three weeks 622. During both phases of the treatment phase 620, the patient may be prescribed a diet plan 623, an exercise regimen 624, and inpatient therapy 625.

In post-treatment phase 630, after discharge, the patient receives pharmaceutical compositions 630a, which include gabapentin titrated up to 400 mg per day for 30 days, decreasing to 0. The patient also receives fortified vitamin B 100 complex daily and a plurality of amino acid supplements. This regimen is interrupted for a second round of treatments, as described above, after three weeks have elapsed from the first round of treatments and restarted thereafter. During post-treatment 630, the patient may also undergo CIWA assessment 630b as needed, outpatient therapy 630c, a diet plan 630d, and an exercise regimen 630e.

In another exemplary methodology, a patient is treated on an inpatient basis for alcohol dependence. Preferably, in this treatment methodology, the interval between treatment episodes, implemented in a series, should be no less than 12 hours and no greater the 24 hours. Depending on a patient's progress with the treatments, he or she may require an additional treatment requiring that would take place on day three of his/her inpatient stay, as described above in an exemplary CIWA-Ar Evaluation Guide.

On day one, the patient is administered 50 mg of hydroxyzine HCL 50 p.o., unless otherwise contraindicated. After at least one-hour, the Selective Chloride Channel Modulator, such as flumazenil, is administered. Prior to Selective Chloride Channel Modulator infusion, two infusion bags are prepared. The first infusion bag comprises 500 cc ½ normal saline (NS) to which thiamine, pyridoxine and other vitamin components are added and the second infusion bag comprises 500 cc ½ NS for clearing the line and for subsequent Selective Chloride Channel Modulator administration. 100 mg of thiamine, 25 mg of pyridoxine, and 5 cc of MVI is preferably added to the first infusion bag. The first infusion bag is administered to the patient at 125 cc/hr (NTE 150 cc/hour) by placing the IV in the antecubital fossa. The IV line should further include the use of a stopcock for clearing of the line and subsequent administration of the Selective Chloride Channel Modulator. Using the stopcock, the line should be washed out with the ½ NS until no further color is seen in the line going to the patient.

Once the line is washed, the Selective Chloride Channel Modulator administration can be initiated. Where the Selective Chloride Channel Modulator is flumazenil, a total dose of 2 mg is given at each treatment episode. The medication should be given by IV bolus as follows: a) 0.1 mg every 3 minutes for two doses, b) 0.2 mg every 3 minutes for two doses; and c) 0.3 mg every 2 minutes until the total dose of 2 mg has been given. If, when increasing dose or decreasing time between doses, discomfort of any kind is observed or reported, the drug administration should be returned to the pre-discomfort level or even returned to initial levels. In one embodiment, the total dose of flumazenil administration is 4 mg for alcohol dependence (two treatment episodes) and 6 mg for patients requiring an additional treatment (e.g. on inpatient day # 3). Parameters of flumazenil administration could be modified in some cases. Quantities can be higher than the 2 mg dose or can be higher than 0.3 mg per administration. Additionally, time periods between administrations can be increased or decreased slightly. Once the flumazenil administration is complete, the vitamin infusion can be reinitiated once the line is cleared with ½ NS. The patient should be monitored for 3 hours post flumazenil administration during which time repeat CIWA-Ar assessments should be performed.

Provided in Tables 3 and 4 below are further details on this specific methodology example.

TABLE 3

Alcohol Dependence Treatment Methodology During 2 Day In-Patient Stay

| Day 1 Time | Day 1 (Admission Day) | Day 2 Time | Day 2 (Discharge) | Post-discharge medications |
|---|---|---|---|---|
| 30 minutes | Negative Urine toxicology. Pre-treatment Medical Assessment | 1 hour | Hydroxyzine HCL 50 mg po Continue Observation & Monitoring for AWS MVI/12, Thiamine, Pyridoxine IV 150 cc, NTE 150 cc/hr. | Hydroxyzine HCL: 50 mg po hs for one Week Gabapentin: Begin day following discharge 900 mg po hs for 30 days then titrate down to 0 days 31-37 ((600 mg for 3 days, 300 mg for 3 days) Fortified Vitamin B Complex: 100 mg po for one Week |

TABLE 3-continued

Alcohol Dependence Treatment Methodology During 2 Day In-Patient Stay

| Day 1 Time | Day 1 (Admission Day) | Day 2 Time | Day 2 (Discharge) | Post-discharge medications |
|---|---|---|---|---|
| 1 hour | Hydroxyzine HCL 50 mg po<br>MVI/12, Thiamine, Pyridoxine IV NTE 150 cc/hr. | 30 mins. | Flumazenil 2 mg IVP per administration schedule | |
| 30 mins. | Flumazenil 2 mg IVP per administration schedule | 3 hours | MVI/12, Thiamine, Pyridoxine IV NTE 150 cc/hr. (Total vitamin infusion of 250 cc-500 cc) Continue Observation & Monitoring Gabapentin 600 mg po May discharge if CIWA-AR <6 Discharge w/ medication instructions and continuing care recommendations | |
| 3 hours | MVI/12, Thiamine, Pyridoxine IV NTE 150 cc/hr. (Total vitamin infusion of 250 cc-500 cc) Continue Observation & Monitoring | | | |
| Bedtime | Gabapentin 300 mg po no later than 21:00 hrs. but after CIWA-Ar assessment Hydroxyzine HCL 50 mg po @ bedtime may repeat with 25 mg as needed for sleep | | If day 3 needed: See inpatient alcohol CIWA-Ar Evaluation Guide to determine need for $3^{rd}$ day. If $3^{rd}$ day needed, refer to Table 4 below | |

TABLE 4

Alcohol Dependence Treatment Methodology During 3 day In-Patient Stay

| Day 1 Time | Day 1 (Admission Day) | Day 2 Time | Day 2 | Day 3 Time | Day 3 (Discharge) | Post-discharge medications |
|---|---|---|---|---|---|---|
| 30 mins. | Negative Urine toxicology Pre-treatment Medical Assessment | 1 hour | Hydroxyzine HCL 50 mg po Continue Observation & Monitoring for AWS MVI/12, Thiamine, Pyridoxine IV 150 cc, NTE 150 cc/hr. | 1 hour | Hydroxyzine HCL 50 mg po Continue Observation & Monitoring for AWS MVI/12, Thiamine, Pyridoxine IV 150 cc, NTE 150 cc/hr. | Hydroxyzine HCL: 50 mg po hs for one week Gabapentin: Begin day following discharge 900 mg po hs for 30 days then titrate down to 0 days 31-37 ((600 mg for 3 days, 300 mg for 3 days) Fortified Vitamin B Complex: 100 mg po for One Week |
| 1 hour | Hydroxyzine HCL 50 mg po MVI/12, Thiamine, Pyridoxine IV NTE 150 cc/hr. | 30 mins. | Flumazenil 2 mg IVP per administration schedule | 30 mins. | Flumazenil 2 mg IVP per administration schedule | |
| 30 mins. | Flumazenil 2 mg IVP per administration schedule | 3 hours | MVI/12, Thiamine, Pyridoxine IV NTE 150 cc/hr. (Total vitamin infusion of | 3 hours | MVI/12, Thiamine, Pyridoxine IV NTE 150 cc/hr. (Total vitamin | |

TABLE 4-continued

Alcohol Dependence Treatment Methodology During 3 day In-Patient Stay

| Day 1 Time | Day 1 (Admission Day) | Day 2 Time | Day 2 | Day 3 Time | Day 3 (Discharge) | Post-discharge medications |
|---|---|---|---|---|---|---|
| | | | 250 cc-500 cc) Continue Observation & Monitoring | | infusion of 250 cc-500 cc) Continue Observation & Monitoring Gabapentin 900 mg po | |
| 3 hours | MVI/12, Thiamine, Pyridoxine IV NTE 150 cc/hr. (Total vitamin infusion of 250 cc-500 cc) Continue Observation & Monitoring | | | | Discharge w/ medication instructions and continuing care recommendations | |
| Bedtime | Gabapentin 300 mg po no later than 21:00 hrs. but after CIWA-Ar assessment Hydroxyzine HCL 50 mg po @ bedtime may repeat with 25 mg as needed for sleep | Bedtime | Gabapentin 600 mg po no later than 21:00 hrs. but after CIWA-Ar assessment Hydroxyzine HCL 50 mg po @ bedtime may repeat with 25 mg as needed for sleep | | | |

In another exemplary methodology, a patient is treated on an outpatient basis for alcohol dependence. Preferably, in this treatment methodology, the interval between treatment episodes, implemented in a series, should be no less than 12 hours and no greater the 24 hours.

On day one, the patient is administered 50 mg of hydroxyzine HCL 50 p.o., unless otherwise contraindicated. After at least one-hour, the Selective Chloride Channel Modulator, such as flumazenil, is administered. Prior to Selective Chloride Channel Modulator infusion, two infusion bags are prepared. The first infusion bag comprises 500 cc ½ normal saline (NS) to which thiamine, pyridoxine and other vitamin components are added and the second infusion bag comprises 500 cc ½ NS for clearing the line and for subsequent Selective Chloride Channel Modulator administration. 100 mg of thiamine, 25 mg of pyridoxine, and 5 cc of MVI is preferably added to the first infusion bag. The first infusion bag is administered to the patient at 125 cc/hr (NTE 150 cc/hour) by placing the IV in the antecubital fossa. The IV line should further include the use of a stopcock for clearing of the line and subsequent administration of the Selective Chloride Channel Modulator. Using the stopcock, the line should be washed out with the ½ NS until no further color is seen in the line going to the patient.

Once the line is washed, the Selective Chloride Channel Modulator administration can be initiated. Where the Selective Chloride Channel Modulator is flumazenil, a total dose of 2 mg is given at each treatment episode. The medication should be given by IV bolus as follows: a) 0.1 mg every 3 minutes for two doses, b) 0.2 mg every 3 minutes for two doses; and c) 0.3 mg every 2 minutes until the total dose of 2 mg has been given. If, when increasing dose or decreasing time between doses, discomfort of any kind is observed or reported, the drug administration should be returned to the pre-discomfort level or even returned to initial levels. In one embodiment, the total dose of flumazenil administration is 4 mg for alcohol dependence (two treatment episodes). Parameters of flumazenil administration could be modified in some cases. Quantities can be higher than the 2 mg dose or can be higher than 0.3 mg per administration. Additionally, time periods between administrations can be increased or decreased slightly. Once the flumazenil administration is complete, the vitamin infusion can be reinitiated once the line is cleared with ½ NS. The patient should be monitored for 3 hours post flumazenil administration during which time repeat CIWA-Ar assessments should be performed.

Provided in Table 5 below are further details on this specific methodology example.

TABLE 5

Alcohol Dependence Treatment Methodology During 2 Day Out-Patient Stay

| Day 1 Time | Day 1 | Day 2 Time | Day 2 | Final discharge medications |
|---|---|---|---|---|
| 30 mins. | Negative Urine toxicology. Pre-treatment Medical Assessment | 1 hour | Hydroxyzine HCL 50 mg po Continue Observation & Monitoring MVI/12, Thiamine, Pyridoxine IV 150 cc, NTE 150 cc/hr. | Hydroxyzine HCL: 50 mg po hs for One Week Gabapentin: Begin day following final discharge 900 mg po hs for 30 days then titrate down to 0 days 31-37 ((600 mg for 3 days, 300 mg for 3 days) Fortified Vitamin B Complex: 100 mg po for One Week |
| 1 hour | Hydroxyzine HCL 50 mg po MVI/12, Thiamine, Pyridoxine IV NTE 150 cc/hr. | 30 mins. | Flumazenil 2 mg IVP per administration schedule | |
| 30 mins. | Flumazenil 2 mg IVP per administration schedule | 3 hours | MVI/12, Thiamine, Pyridoxine IV NTE 150 cc/hr. (Total vitamin infusion of 250 cc-500 cc) Continue Observation & Monitoring Gabapentin 600 mg po May discharge if CIWA-AR <6 Discharge w/ medication instructions and continuing care recommendations | |
| 3 hours | MVI/12, Thiamine, Pyridoxine IV NTE 150 cc/hr. (Total vitamin infusion of 250 cc-500 cc) Continue Observation & Monitoring May discharge if CIWA-AR <6 Discharge w/ medication instructions and scheduled time for day 2 treatment | | | |
| Bedtime | Gabapentin 300 mg po no later than 21:00 hrs. Hydroxyzine HCL 50 mg po @ bedtime may repeat with 25 mg as needed for sleep | | | |

In another exemplary methodology, a patient is treated on an inpatient or outpatient basis for stimulant dependence. Preferably, in this treatment methodology, the interval between treatment episodes, implemented in a series, should be no less than 12 hours and no greater the 24 hours.

On day one, the patient is administered 50 mg of hydroxyzine HCL 50 p.o., unless otherwise contraindicated. After at least one-hour, the Selective Chloride Channel Modulator, such as flumazenil, is administered. Prior to Selective Chloride Channel Modulator infusion, two infusion bags are prepared. The first infusion bag comprises 500 cc ½ normal saline (NS) to which thiamine, pyridoxine and other vitamin components are added and the second infusion bag comprises 500 cc ½ NS for clearing the line and for subsequent Selective Chloride Channel Modulator administration. 100 mg of thiamine, 25 mg of pyridoxine, and 5 cc of MVI is preferably added to the first infusion bag. The first infusion bag is administered to the patient at 125 cc/hr (NTE 150 cc/hour) by placing the IV in the antecubital fossa. The IV line should further include the use of a stopcock for clearing of the line and subsequent administration of the Selective Chloride Channel Modulator. Using the stopcock, the line should be washed out with the ½ NS until no further color is seen in the line going to the patient.

Once the line is washed, the Selective Chloride Channel Modulator administration can be initiated. Where the Selective Chloride Channel Modulator is flumazenil, a total dose of 2 mg is given at each treatment episode. The medication should be given by IV bolus as follows: a) 0.1 mg every 3 minutes for two doses, b) 0.2 mg every 3 minutes for two doses; and c) 0.3 mg every 2 minutes until the total dose of 2 mg has been given. If, when increasing dose or decreasing time between doses, discomfort of any kind is observed or reported, the drug administration should be returned to the pre-discomfort level or even returned to initial levels. In one embodiment, the total dose of flumazenil administration is 6 mg for the first treatment cycle (three treatment episodes) and 4 mg for the second treatment cycle (two treatment episodes). Parameters of flumazenil administration could be modified in some cases. Quantities can be higher than the 2 mg dose or can be higher than 0.3 mg per administration. Additionally, time periods between administrations can be increased or decreased slightly. Once the flumazenil administration is complete, the vitamin infusion can be reinitiated once the line is cleared with ½ NS. The patient should be monitored for 3 hours post flumazenil administration during which time repeat CIWA-Ar assessments should be performed.

Provided in Tables 6 and 7 below are further details on this specific methodology example.

TABLE 6

Stimulant Dependence Treatment Methodology
Cycle 1 - During 3 day In-Patient/Out-Patient Stay

| Day 1 Time | Day 1 (Admission Day) | Day 2 Time | Day 2 | Day 3 Time | Day 3 | Post-discharge medications |
|---|---|---|---|---|---|---|
| 30 mins. | Negative Urine toxicology. Pre-treatment Medical Assessment | 1 hour | Hydroxyzine HCL 50 mg po Continue Observation & Monitoring MVI/12, Thiamine, Pyridoxine IV 150 cc, NTE 150 cc/hr. | 1 hour | Hydroxyzine HCL 50 mg po Continue Observation & Monitoring MVI/12, Thiamine, Pyridoxine IV 150 cc, NTE 150 cc/hr. | Hydroxyzine HCL: 50 mg po hs for one week Gabapentin: Begin day following discharge 900 mg po hs for 2 days and days 3 to evening before treatment cycle 2 1200 mg po hs Fortified Vitamin B Complex: 100 mg po for One Week |
| 1 hour | Hydroxyzine HCL 50 mg po MVI/12, Thiamine, Pyridoxine IV NTE 150 cc/hr. | 30 mins. | Flumazenil 2 mg IVP per admin. schedule | 30 mins. | Flumazenil 2 mg IVP per admin. schedule | |
| 30 mins. | Flumazenil 2 mg IVP per admin. schedule | 3 hours | MVI/12, Thiamine, Pyridoxine IV NTE 150 cc/hr. (Total vitamin infusion of 250 cc-500 cc) Continue Observation & Monitoring Gabapentin 600 mg po | 3 hours | MVI/12, Thiamine, Pyridoxine IV NTE 150 cc/hr. (Total vitamin infusion of 250 cc-500 cc) Continue Observation & Monitoring Gabapentin 600 mg po Discharge w/ medication instruction and continuing care recommend. | |
| 3 hours | MVI/12, Thiamine, Pyridoxine IV NTE 150 cc/hr. (Total vitamin infusion of 250 cc-500 cc) Continue Observation & Monitoring | | | | | |
| Bedtime | Gabapentin 300 mg po no later than 21:00 hrs. Hydroxyzine HCL 50 mg po @ bedtime may repeat with 25 mg as needed for sleep | | | | | |

TABLE 7

Stimulant Dependence Treatment Methodology
Cycle 2 - During 2 day In-Patient/Out-Patient Stay

| Day 1 Time | Day 1 (Admission Day) | Day 2 Time | Day 2 (Discharge) | Post-discharge medications |
|---|---|---|---|---|
| 30 mins. | Negative Urine toxicology Pre-treatment Medical Assessment | 1 hour | Hydroxyzine HCL 50 mg po Continue Observation & Monitoring MVI/12, Thiamine, Pyridoxine IV 150 cc, NTE 150 cc/hr. | Gabapentin: Continue 1200 mg po hs for one week then titrate down to 0 days 8-16 (900 mg for 3 days, 600 mg for 3 days, 300 mg for 3 days) |
| 1 hour | Hydroxyzine HCL 50 mg po MVI/12, Thiamine, Pyridoxine IV NTE 150 cc/hr. | 30 mins. | Flumazenil 2 mg IVP per administration schedule | |
| 30 mins. | Flumazenil 2 mg IVP per admin. schedule | 3 hours | MVI/12, Thiamine, Pyridoxine IV NTE 150 cc/hr. (Total vitamin infusion of 250 cc-500 cc) Continue Observation & Monitoring | |
| 3 hours | MVI/12, Thiamine, Pyridoxine IV NTE 150 cc/hr. (Total vitamin infusion of 250 cc-500 cc) Continue Observation & Monitoring | | | |
| Bedtime | Gabapentin 300 mg po no later than 21:00 hrs. Hydroxyzine HCL 50 mg po @ bedtime may repeat with 25 mg as needed for sleep | Bedtime | Gabapentin 600 mg po no later than 21:00 hrs. Hydroxyzine HCL 50 mg po @ bedtime may repeat with 25 mg as needed for sleep | |

In another exemplary methodology, a patient is treated on an inpatient or outpatient basis for stimulant abuse or on an inpatient or outpatient basis for stimulant and alcohol abuse.

After a patient has been properly screened and admitted to a treatment facility for in-patient treatment, a patient undergoes a first treatment cycle which comprises a series of treatments over a period of three days. On the first day, the patient is administered hydroxyzine and a selective chloride channel modulator, preferably flumazenil. In one embodiment, the patient is administered hydroxyzine HCL 50 mg p.o. one hour before flumazenil infusion. A medical practitioner records the time of hydroxyzine HCL administration and all subsequent medication administrations.

Two infusion bags are prepared. A first infusion bag comprises a 500 cc Ringers Lactate Solution to which thiamine and multivitamin components are added, and a second infusion bag comprises a 500 cc Ringers Lactate Solution for clearing of the line following flumazenil administration. To the first infusion bag is added thiamine 250 mg and a 5 cc MVI vial. An IV is inserted using a stopcock for clearing of the line following each dose of flumazenil and subsequent administration of flumazenil. A heparin-lock may be placed in patients admitted on an in-patient status. The intravenous vitamin infusion is administered at a rate between 200 and 250 cc/hour. A medical practitioner preferably obtains and records the patient's pulse, blood pressure and respiratory rate before infusion and every 3-5 minutes following flumazenil administration.

The medical practitioner should use the stopcock, stop the flow of vitamins and washout out the line going to the patient with the Ringer's Lactate Solution until no further color is seen in the line going to the patient. Flumazenil should then be administered, as described below, clearing the line with the Ringer's Lactate Solution after each dose of flumazenil.

In a freely flowing intravenous infusion, flumazenil should be administered via IV over about 1 minute as follows:
  0.1 mg every 3 minutes for two doses.
  0.2 mg every 3 minutes for two doses.
  0.3 mg every 2 minutes until the total dose of 2 mg has been given.

If, when increasing dose or decreasing time between doses, discomfort of any kind is observed or reported, the drug administration should be returned to the pre-discomfort level or even returned to initial levels. The standard total dose of flumazenil administration is 6 mg for the first treatment cycle and 4 mg for second treatment cycle giving a total dose of 10 mg.

Once the flumazenil administration is complete, the vitamin infusion can continue. The patient is to be medically monitored for three hours post flumazenil administration. During the monitoring process, CIWA-Ar assessment should be repeated if treating for combination stimulant and alcohol dependence.

At bedtime, the patient is administered gabapentin 300 mg orally and hydroxyzine HCL at bedtime if a medical practitioner determines a patient needs it for sleep.

On the second day, the patient is administered, as detailed above, hydroxyzine and flumazenil. At bedtime, the patient is administered gabapentin 600 mg p.o and hydroxyzine HCL 50 mg orally if needed for sleep.

On the third day, the patient is administered, as detailed above, hydroxyzine and flumazenil. The patient is instructed to take 900 mg of gabapentin at bedtime and hydroxyzine HCL 50 mg orally if needed for sleep. Thereafter, the patient is instructed to take 1200 mg of gabapentin at bedtime if needed and hydroxyzine HCL 50 mg orally if needed for sleep. Before discharge, patients are prescribed the following medication: hydroxyzine HCL (50 mg p.o. hs for one week), gabapentin (beginning the day following the first treatment cycle, 1200 mg is to be taken at bedtime for until the next treatment cycle and continued at 1200 mg for one week following the second treatment cycle and then tapered to zero), multivitamin (once daily p.o. for one month), and thiamine (250 mg p.o. daily for one month).

After a period of time, preferably between 21 and 28 days, the patient is reassessed in a second treatment cycle. In one embodiment, patients who cannot engage in treatment a pre-designated period, such as 28 days, the patient will be restarted on the first treatment cycle. The reassessment is conducted using CIWA-Ar in cases where the patient is being treated for a combination of stimulant and alcohol dependence. If appropriate, the patient is then instructed to gabapentin 1200 mg per day is continued through this second treatment cycle.

In a case where a patient is being treated on an out-patient basis, after a patient has been properly screened, a patient undergoes a first treatment cycle which comprises a series of treatments over a period of three days. On the first day, the patient is administered hydroxyzine and a Selective Chloride Channel Modulator, preferably flumazenil. In one embodiment, the patient is administered hydroxyzine HCL 50 mg p.o. one hour before flumazenil infusion in a manner as described above. After completing the infusion, the patient is administered gabapentin 300 mg orally and the CIWA-Ar assessment is repeated if treating for a combination of stimulant and alcohol dependence. The patient may be released when the CIWA-AR score is <6. The patient is provided with 50 mg hydroxyzine HCL and instructions to take before bedtime if needed for sleep.

On the second day, the patient is administered hydroxyzine and a Selective Chloride Channel Modulator, preferably flumazenil. In one embodiment, the patient is administered hydroxyzine HCL 50 mg p.o. one hour before flumazenil infusion in a manner as described above. After completing the infusion, the patient is administered gabapentin 600 mg p.o. and the CIWA-Ar assessment is repeated if treating for a combination of stimulant and alcohol dependence. The patient may be released when the CIWA-AR score is <6. The patient is provided with 50 mg hydroxyzine HCL and instructions to take before bedtime if needed for sleep.

On the third day, the patient is administered hydroxyzine and a Selective Chloride Channel Modulator, preferably flumazenil. In one embodiment, the patient is administered hydroxyzine HCL 50 mg p.o. one hour before flumazenil infusion in a manner as described above. After completing the infusion, the patient is administered gabapentin 900 mg p.o. and the CIWA-Ar assessment is repeated if treating for a combination of stimulant and alcohol dependence. The patient may be released when the CIWA-AR score is <6.

At the end of the third day of treatment, patients are prescribed the following medication: hydroxyzine HCL (50 mg p.o. hs for one week), gabapentin (beginning the day following the first treatment cycle, 1200 mg is to be taken at bedtime for until the next treatment cycle and continued at 1200 mg for one week following the second treatment cycle and then tapered to zero), multivitamin (once daily p.o. for one month), and thiamine (250 mg p.o. daily for one month).

After a period of time, preferably between 21 and 28 days, the patient is reassessed in a second treatment cycle. In one embodiment, patients who cannot engage in treatment a pre-designated period, such as 28 days, the patient will be restarted on the first treatment cycle. The reassessment is conducted using CIWA-Ar in cases where the patient is being treated for a combination of stimulant and alcohol dependence.

Provided in Tables 8 and 9 below are further details on this specific methodology example.

TABLE 8

Procedures during Treatment Cycle 1

| Day 1 Time | Day 1 (Admission) | Day 2 Time | Day 2 | Day 3 Time | Day 3 (Discharge) | Post-discharge medications |
|---|---|---|---|---|---|---|
| 30 min. | Negative Urine toxicology Pre-treatment Medical Assessment | 30 min. | Negative Urine toxicology (out-patient only) | 30 min. | Negative Urine toxicology (out-patient only) | Hydroxyzine HCL: 50 mg po hs for one Week Gabapentin 300 mg day 1, 600 mg day 2, |
| 1 hour | Hydroxyzine HCL 50 mg po Continue Observation | 1 hour | Hydroxyzine HCL 50 mg po Continue Observation & | 1 hour | Hydroxyzine HCL 50 mg po Continue Observation & | 900 mg day 3, 1200 mg days 4-30, 900 mg days 31-33, |

TABLE 8-continued

Procedures during Treatment Cycle 1

| Day 1 Time | Day 1 (Admission) | Day 2 Time | Day 2 | Day 3 Time | Day 3 (Discharge) | Post-discharge medications |
|---|---|---|---|---|---|---|
|  | & Monitoring MVI/12, Thiamine, IV 200-250 cc/hr. |  | Monitoring MVI/12, Thiamine, IV 200-250 cc/hr. |  | Monitoring MVI/12, Thiamine, IV 200-250 cc/hr. | 600 mg days 34-36, and 300 mg days 37-39 |
| 30 min. | Flumazenil IVP per admin. schedule (cumulative dose of 2 mg) | 30 min. | Flumazenil IVP per administration schedule (cumulative dose of 2 mg) | 30 min. | Flumazenil IVP per admin. schedule (cumulative dose of 2 mg) | Multivitamin and Thiamine 100 mg: po for one month |
| 3 hours | Complete MVI/12, Thiamine, IV 150 cc-200 cc/hr. Continue Observation & Monitoring | 3 hours | Complete MVI/12, Thiamine, IV 150 cc-200 cc/hr. Continue Observation & Monitoring | 3 hours | Complete MVI/12, Thiamine, IV 150 cc-200 cc/hr. Continue Observation & Monitoring Gabapentin 900 mg po Discharge w/ medication, continuing care recommendations and appointment for treatment cycle 2 |  |
| Bedtime | Gabapentin 300 mg po no later than 21:00 hrs. but after CIWA-Ar assessment Hydroxyzine HCL 50 mg po @ bedtime may repeat with 25 mg as needed for sleep | Bedtime | Gabapentin 600 mg po no later than 21:00 hrs. but after CIWA-Ar assessment Hydroxyzine HCL 50 mg po @ bedtime may repeat with 25 mg as needed for sleep |  |  |  |

TABLE 9

Procedures during Treatment Cycle 2

| Day 1 Time | Day 1 (Admission) | Day 2 Time | Day 2 (Discharge) | Post-discharge medications |
|---|---|---|---|---|
| 30 min. | Negative Urine toxicology Pre-treatment Medical Assessment | 30 min. | Negative Urine toxicology (screen out-patient only) | Gabapentin 300 mg day 1, 600 mg day 2, 900 mg day 3, 1200 mg days 4-30, 900 mg days 31-33, 600 mg days 34-36, and 300 mg days 37-39 |
| 1 hour | Hydroxyzine HCL 50 mg po Continue Observation & Monitoring MVI/12, Thiamine, IV 200-260 cc/hr. | 1 hour | Hydroxyzine HCL 50 mg po Continue Observation & Monitoring MVI/12, Thiamine, IV 200-250 cc/hr. |  |
| 30 min. | Flumazenil IVP per administration schedule (cumulative dose of 2 mg) | 30 min. | Flumazenil IVP per administration schedule (cumulative dose of 2 mg) |  |
| 3 hours | MVI/12, Thiamine, IV 200-250 cc/hr. Continue Observation & Monitoring | 3 hours | MVI/12, Thiamine, IV 200-250 cc/hr. Continue Observation & Monitoring |  |
| Bedtime | Gabapentin 1200 mg po no later |  | Discharge w/ medication |  |

TABLE 9-continued

Procedures during Treatment Cycle 2

| Day 1 Time | Day 1 (Admission) | Day 2 Time | Day 2 (Discharge) | Post-discharge medications |
|---|---|---|---|---|
| | than 21:00 hrs. | | instructions and continuing care recommendations | |

In another exemplary methodology, a patient is treated on an inpatient basis for alcohol abuse. After a patient has been properly screened and admitted to a treatment facility for in-patient treatment, a patient undergoes a first treatment cycle, which comprises a series of treatments over a period of two to three days. Preferably the interval between treatment episodes should be no less than 12 hours and no greater than 30 hours.

On the first day, the patient is administered hydroxyzine and a Selective Chloride Channel Modulator, preferably flumazenil. In one embodiment, the patient is administered hydroxyzine HCL 50 mg p.o. one hour before flumazenil infusion. A medical practitioner records the time of hydroxyzine HCL administration and all subsequent medication administrations.

Two infusion bags are prepared. A first infusion bag comprises a 500 cc Ringers Lactate Solution to which thiamine and multivitamin components are added, and a second infusion bag comprises a 500 cc Ringers Lactate Solution for clearing of the line following flumazenil administration. To the first infusion bag is added thiamine 100 mg and a 5 cc MVI vial. An IV is inserted using a stopcock for clearing of the line following each dose of flumazenil and subsequent administration of flumazenil. A heparin-lock may be placed in patients admitted on an in-patient status. The intravenous vitamin infusion is administered at a rate between 150 and 200 cc/hour. A medical practitioner preferably obtains and records the patient's pulse, blood pressure and respiratory rate before infusion and every 3-5 minutes following flumazenil administration.

The medical practitioner should use the stopcock, stop the flow of vitamins and washout out the line going to the patient with the Ringer's Lactate Solution until no further color is seen in the line going to the patient. Flumazenil should then be administered, as described below, clearing the line with the Ringer's Lactate Solution after each dose of flumazenil.

In a freely flowing intravenous infusion, flumazenil should be administered via IV over about 1 minute as follows:
 0.1 mg every 3 minutes for two doses.
 0.2 mg every 3 minutes for two doses.
 0.3 mg every 2 minutes until the total dose of 2 mg has been given.

If, when increasing dose or decreasing time between doses, discomfort of any kind is observed or reported, the drug administration should be returned to the pre-discomfort level or even returned to initial levels. The standard total dose of flumazenil administration is 4 mg for two treatment episodes (treatment days one and two) and 6 mg for three treatment episodes (treatment days one, two and three).

Once the flumazenil administration is complete, the vitamin infusion can continue. The patient is to be medically monitored for three hours post flumazenil administration. During the monitoring process, CIWA-Ar assessment should be repeated.

At bedtime, such as around 9 p.m., the patient is administered gabapentin 300 mg p.o. and 50 mg p.o. hs of hydroxyzine HCL. The patient is also assessed with the CIWA-Ar.

On the second day, the patient is administered, as detailed above, hydroxyzine and flumazenil. The patient is administered gabapentin 600 mg p.o prior to discharge and 50 mg p.o. hs hydroxyzine HCL. Depending on a patients' CIWA-Ar score, some patients may need a third day of treatment. If a third treatment episode, i.e. a third day, is required, the patient is administered 600 mg p.o. gabapentin prior to 9 p.m. and 900 mg gabapentin p.o. prior to discharge.

At the end of the final day of treatment, patients are prescribed the following medication: hydroxyzine HCL (50 mg p.o. hs for one week), gabapentin (beginning the day following the first treatment cycle, 900 mg p.o. hs for 30 days, 600 mg p.o. hs for days 31-33, and 300 mg p.o. hs for days 34-37), multivitamin (once daily p.o. for one month), and thiamine (100 mg p.o. daily for one month).

TABLE 10

Treatment for Alcohol Dependence
Administration during 2 day in-patient stay

| Day 1 Time | Day 1 (Admission Day) | Day 2 Time | Day 2 (Discharge) | Post-discharge Medications |
|---|---|---|---|---|
| 30 min. | Negative Urine toxicology. Pre-treatment Medical Assessment | 1 hour | Hydroxyzine HCL 50 mg po Continue Observation & Monitoring MVI/12, Thiamine, IV 125 cc-150 cc/hr | Hydroxyzine HCL: 50 mg po hs for One week Gabapentin: Begin day following discharge 900 mg po hs for 30 days then titrate down to 0 days 31-37 (600 mg for 3 days, 300 mg for |
| 1 hour | Hydroxyzine HCL 50 mg po MVI/12, Thiamine, IV 125 cc-150 cc/hr. | 30 min. | Flumazenil 2 mg IVP per administration schedule | |

TABLE 10-continued

Treatment for Alcohol Dependence
Administration during 2 day in-patient stay

| Day 1 Time | Day 1 (Admission Day) | Day 2 Time | Day 2 (Discharge) | Post-discharge Medications |
|---|---|---|---|---|
| 30 min. | Flumazenil 2 mg IVP per administration schedule | 3 hours | MVI/12, Thiamine, IV 125 cc-150 cc/hr. (Total vitamin infusion of 250 cc-500 cc) Continue Observation & Monitoring Gabapentin 600 mg po | 3 days) Multivitamin and Thiamine 100 mg: po for One month |
| 3 hours | MVI/12, Thiamine IV 125 cc-150 cc/hr. (Total vitamin infusion of 250 cc-500 cc) Continue Observation & Monitoring | | May discharge if CIWA-AR <6 Discharge w/ medication instructions and continuing care recommendations If day 3 needed: See Table 11 | |
| Bedtime | Gabapentin 300 mg po no later than 21:00 hrs. but after CIWA-Ar assessment Hydroxyzine HCL 50 mg po @ bedtime may repeat with 25 mg as needed for sleep | | | |

TABLE 11

Treatment for Alcohol Dependence During 3 day in-patient stay
(Day 3 required if CIWA ≧10 on day 1 or day 2 or CIWA >6 post infusion on day 2)

| Day 1 Time | Day 1 (Admission) | Day 2 Time | Day 2 | Day 3 Time | Day 3 (Discharge) | Post-discharge medications |
|---|---|---|---|---|---|---|
| 30 min. | Negative Urine toxicology Pre-treatment Medical Assessment | 1 hour | Hydroxyzine HCL 50 mg po Continue Observation & Monitoring MVI/12, Thiamine, IV 125 cc-150 cc/hr. | 1 hour | Hydroxyzine HCL 50 mg po Continue Observation & Monitoring MVI/12, Thiamine, IV 125 cc-150 cc/hr. | Hydroxyzine HCL: 50 mg po hs for One Week Gabapentin: Begin day following discharge 900 mg po hs for 30 days then taper days 31-37 (600 mg for 3 days, 300 mg for 3 days) Multivitamin and Thiamine 100 mg: po for One Month |
| 1 hour | Hydroxyzine HCL 50 mg po MVI/12, Thiamine, IV 125-150 cc/hr. | 30 min. | Flumazenil 2 mg IVP per administration schedule | 30 min. | Flumazenil 2 mg IVP per admin. schedule | |
| 30 min. | Flumazenil 2 mg IVP per admin. schedule | 3 hours | MVI/12, Thiamine, IV 125 cc-150 cc/hr. (Total vitamin infusion of 250 cc-500 cc) Continue Observation & Monitoring | 3 hours | MVI/12, Thiamine, IV 125 cc-150 cc/hr. (Total vitamin infusion of 250 cc-500 cc) Continue Observation & Monitoring Gabapentin 900 mg po Discharge w/ medication instructions and | |
| 3 hours | MVI/12, Thiamine, IV 125 cc-150 cc/hr. Continue | | | | | |

TABLE 11-continued

Treatment for Alcohol Dependence During 3 day in-
patient stay
(Day 3 required if CIWA ≧10 on day 1 or day 2 or CIWA >6 post
infusion on day 2)

| Day 1 Time | Day 1 (Admission) | Day 2 Time | Day 2 | Day 3 Time | Day 3 (Discharge) | Post-discharge medications |
|---|---|---|---|---|---|---|
| | Observation & Monitoring | | | | | continuing care recommendations |
| Bedtime | Gabapentin 300 mg po no later than 21:00 hrs. but after CIWA-Ar assessment Hydroxyzine HCL 50 mg po @ bedtime may repeat with 25 mg as needed for sleep | Bedtime | Gabapentin 600 mg po no later than 21:00 hrs. but after CIWA-Ar assessment Hydroxyzine HCL 50 mg po @ bedtime may repeat with 25 mg as needed for sleep | | | |

In another exemplary methodology, a patient is treated on an outpatient basis for alcohol abuse. After a patient has been properly screened, a patient undergoes a first treatment cycle, which comprises a series of treatments over a period of two days. Preferably the interval between treatment episodes should be no less than 12 hours and no greater than 30 hours.

On the first day, the patient is administered hydroxyzine and a Selective Chloride Channel Modulator, preferably flumazenil. In one embodiment, the patient is administered hydroxyzine HCL 50 mg p.o. one hour before flumazenil infusion. A medical practitioner records the time of hydroxyzine HCL administration and all subsequent medication administrations.

Two infusion bags are prepared. A first infusion bag comprises a 500 cc Ringers Lactate Solution to which thiamine and multivitamin components are added, and a second infusion bag comprises a 500 cc Ringers Lactate Solution for clearing of the line following flumazenil administration. To the first infusion bag is added thiamine 100 mg and a 5 cc MVI vial. An IV is inserted using a stopcock for clearing of the line following each dose of flumazenil and subsequent administration of flumazenil. A heparin-lock may be placed in patients admitted on an in-patient status. The intravenous vitamin infusion is administered at a rate between 150 and 200 cc/hour. A medical practitioner preferably obtains and records the patient's pulse, blood pressure and respiratory rate before infusion and every 3-5 minutes following flumazenil administration.

The medical practitioner should use the stopcock, stop the flow of vitamins and washout out the line going to the patient with the Ringer's Lactate Solution until no further color is seen in the line going to the patient. Flumazenil should then be administered, as described below, clearing the line with the Ringer's Lactate Solution after each dose of flumazenil.

In a freely flowing intravenous infusion, flumazenil should be administered via IV over about 1 minute as follows:

0.1 mg every 3 minutes for two doses.

0.2 mg every 3 minutes for two doses.

0.3 mg every 2 minutes until the total dose of 2 mg has been given.

If, when increasing dose or decreasing time between doses, discomfort of any kind is observed or reported, the drug administration should be returned to the pre-discomfort level or even returned to initial levels. The standard total dose of flumazenil administration is 4 mg for two treatment episodes (treatment days one and two).

Once the flumazenil administration is complete, the vitamin infusion can continue. The patient is to be medically monitored for three hours post flumazenil administration. During the monitoring process, CIWA-Ar assessment should be repeated.

Prior to releasing the patient after treatment cycle one, the patient assessed with the CIWA-Ar and released if the score is less than 6. The patient is administered gabapentin 300 mg p.o. The patient is also instructed to take 50 mg p.o. hs of hydroxyzine HCL before bedtime.

On the second day, the patient is administered, as detailed above, hydroxyzine and flumazenil. The patient is assessed using CIWA-Ar and administered gabapentin 600 mg p.o prior to discharge.

At the end of the final day of treatment, patients are prescribed the following medication: hydroxyzine HCL (50 mg p.o. hs for one week), gabapentin (beginning the day following the first treatment cycle, 900 mg p.o. hs for 30 days, 600 mg p.o. hs for days 31-33, and 300 mg p.o. hs for days 34-37), multivitamin (once daily p.o. for one month), and thiamine (100 mg p.o. daily for one month).

TABLE 13

Treatment for Alcohol Dependence
Administration during 2 day out-patient treatment

| Day 1 Time | Day 1 | Day 2 Time | Day 2 | Final Discharge Medications |
|---|---|---|---|---|
| 30 min. | Negative Urine toxicology Pre-treatment Medical Assessment | 30 min. | Negative Urine toxicology | Hydroxyzine HCL: 50 mg po hs for one week Gabapentin: |
| 1 hour | Hydroxyzine HCL 50 mg po Continue Observation & Monitoring MVI/12, Thiamine, IV 125 cc-150 cc/hr. | 1 hour | Hydroxyzine HCL 50 mg po Continue Observation & Monitoring MVI/12, Thiamine, IV 150 cc-200 cc/hr | Begin day following discharge 900 mg po hs for 30 days then taper to 0 days 31-37 (600 mg for 3 days, 300 mg for |
| 30 min. | Flumazenil IVP per administration schedule (cumulative dose of 2 mg) | 30 min. | Flumazenil IVP per administration schedule (cumulative dose of 2 mg) | 3 days) Multivitamin and Thiamine 100 mg: po for One month |
| 3 hours | Complete MVI/12, Thiamine IV 150 cc-200 cc/hr. Continue Observation & Monitoring Gabapentin 300 mg po | 3 hours | Complete MVI/12, Thiamine, IV 150 cc-200 cc/hr. Continue Observation & Monitoring Gabapentin 600 mg po | |
| Release to accompanying person | May discharge if CIWA-AR <6 Discharge w/ medication instructions and scheduled time for day 2 treatment | | May discharge if CIWA-AR <6 Discharge w/ medication instructions and continuing care recommendations | |
| Bedtime | Hydroxyzine HCL 50 mg po @ bedtime may repeat with 25 mg as needed for sleep | | | |

In another exemplary methodology, a patient is treated for alcohol dependence. Preferably, in this treatment methodology, the interval between treatment episodes, implemented in a series, should be no less than 12 hours and no greater the 24 hours.

On day one, the patient is administered 50 mg of hydroxyzine HCL 50 p.o., unless otherwise contraindicated. After at least one-hour, the Selective Chloride Channel Modulator, such as flumazenil, is administered. Prior to Selective Chloride Channel Modulator infusion, two infusion bags are prepared. The first infusion bag comprises 500 cc ½ normal saline (NS) to which thiamine, pyridoxine and other vitamin components are added and the second infusion bag comprises 500 cc ½ NS for clearing the line and for subsequent Selective Chloride Channel Modulator administration. 100 mg of thiamine, 25 mg of pyridoxine, and 5 cc of MVI is preferably added to the first infusion bag. The first infusion bag is administered to the patient at 125 cc/hr (NTE 150 cc/hour) by placing the IV in the antecubital fossa. The IV line should further include the use of a stopcock for clearing of the line and subsequent administration of the Selective Chloride Channel Modulator. Using the stopcock, the line should be washed out with the ½ NS until no further color is seen in the line going to the patient.

Once the line is washed, the Selective Chloride Channel Modulator administration can be initiated. Where the Selective Chloride Channel Modulator is flumazenil, a total dose of 2 mg is given at each treatment episode. The medication should be given by IV bolus as follows: a) 0.1 mg every 3 minutes for two doses, b) 0.2 mg every 3 minutes for two doses; and c) 0.3 mg every 2 minutes until the total dose of 2 mg has been given. If, when increasing dose or decreasing time between doses, discomfort of any kind is observed or reported, the drug administration should be returned to the pre-discomfort level or even returned to initial levels. In one embodiment, the total dose of flumazenil administration is 6 mg for the first treatment cycle (three treatment episodes) and 4 mg for the second treatment cycle (two treatment episodes). Parameters of flumazenil administration could be modified in some cases. Quantities can be higher than the 2 mg dose or can be higher than 0.3 mg per administration. Additionally, time periods between administrations can be increased or decreased slightly. Once the flumazenil administration is complete, the vitamin infusion can be reinitiated once the line is cleared with ½ NS. The patient should be monitored for 3 hours post flumazenil administration during which time repeat CIWA-Ar assessments should be performed.

Provided in Tables 7 and 8 below are further details on this specific methodology example.

In another embodiment of the present invention, a methodology is provided for the use and administration of a Selective Chloride Channel Modulator, such as flumazenil, for the treatment of cravings for alcohol and stimulants. If administered in accordance with the general methodology described above, a therapeutically effective amount of the compound is maintained in the patient, thereby significantly reducing cravings for alcohol and stimulants. The invention also provides for the administration of flumazenil without significant side effects.

In another embodiment of the present invention a methodology is provided that relates to the use and administration of a therapeutically effective quantity of a Selective Chloride Channel Modulator, such as flumazenil, for the treatment of cravings of psychostimulants, reducing withdrawal symptoms during detoxification and treating addiction of psychostimulants and with improvement of cognitive ability, mental clarity, and focus. If administered in accordance with the methodology of the present invention, a therapeutically effective amount of the drug is maintained in the patient thereby significantly reducing cravings for psychostimulants.

The invention also provides for the administration of a Selective Chloride Channel Modulator so as to reduce, and in some cases, eliminate withdrawal symptoms and to generally treat addiction to psychostimulants. Preferably, a drug in the class of Selective Chloride Channel Modulator, such as flumazenil, is administered in multiple dosages for a predetermined time period until a therapeutically effective quantity is administered for the reduction of cravings for psychostimulants.

In another embodiment of the present invention a methodology is described for the use and administration of a therapeutically effective quantity of a Selective Chloride Channel Modulator, such as flumazenil, for the reduction in patient dropout rates both during the administration of the treatment and after the treatment. When administered in accordance with the methodology of the present invention, a therapeutically effective amount of the compound is maintained in the patient, thereby significantly reducing cravings for alcohol and certain stimulants, resulting in lower patient dropout rates. Such dosing also provides for administration of flumazenil with fewer side effects. At these low dosage levels, the treatment is still effective for reducing patient dropout rates while also being therapeutically effective.

The following examples demonstrate the invention and must not be considered to limit the scope thereof.

Example 1

Treatment of Patients with Flumazenil in Multiple Dosages at Predetermined Time Periods 1.1 Experimental Protocol 64 alcoholics (51 males and 13 females) voluntarily entered a treatment program to discontinue the use of alcohol. The patients were provided the appropriate information and the corresponding informed consent form was obtained from them. The patients were warned not to drink alcohol the morning on which the treatment was to be carried out to enable better evaluation of the withdrawal symptoms. Table 14 summarizes the characteristics of the patients treated associated with alcohol use.

TABLE 14

Characteristics of Patients Associated with Alcohol Use

| CHARACTERISTICS | MEAN | STANDARD DEVIATION | MINI-MUM | MAXI-MUM |
| --- | --- | --- | --- | --- |
| AGE (YEARS) | 42.7 | 10.2 | 20 | 75 |
| AGE AT BEGINNING OF DAILY ALCOHOL USE (YEARS) | 24.6 | 10.2 | 6 | 71 |
| DAILY UNITS OF ALCOHOL INTAKE | 24.9 | 15.4 | 4 | 73 |
| GAMMA-GLUTAMYL TRANSPEPTIDASE (GGT) | 159.1 | 227.2 | 12 | 1.230 |
| CORPUSCULAR VOLUME (RBC) | 97.8 | 6.4 | 72 | 111 |
| NUMBER OF PREVIOUS DETOXIFICATIONS | 1.6 | 1.2 | 0 | 5 |

(note: 85% consumed alcohol daily and 39.1% consumed benzodiazepines daily)

Before starting the treatment, the patients underwent a complete medical and psychological examination. The monitoring of the patients throughout the morning included a complete blood count, a biochemical profile [creatinine, glucose, blood urea nitrogen (BUN), cholesterol (HDL and LDL), triglycerides, alkaline phosphatase, LDH (lactic dehydrogenase) and total proteins], hepatic function tests [GOT, GPT, GGT, bilirubin), electrocardiogram and, if need be, pregnancy test and x-ray examination. The exclusion criteria applied included acute or uncompensated illnesses, as well as the taking of any drug contraindicated with flumazenil. No patient was excluded after the pre-admission interview and the tests performed. Admission of one patient was postponed until his cardiac pathology was checked.

Before and after the administration of flumazenil, the withdrawal symptomatology was measured using the CIWA-A evaluation (Adinoff et al., Medical Toxicology 3:172-196 (1988)), as well as heart rate and blood pressure. Table 15 presents the treatment protocol followed during hospitalization.

TABLE 15

Treatment Protocol Followed During Hospitalization.

| TIME | DAY OF ADMISSION | DAY 2 | DAY 3 (DISCHARGE) |
| --- | --- | --- | --- |
| 9:00 a.m. | | Clomethiazole 192 mg<br>Vitamin B Complex<br>Piracetam 3 g (oral)<br>Drink with vitamins,<br>minerals, proteins, and<br>amino acids | Clomethiazole 192 mg<br>Vitamin B Complex<br>Piracetam 3 g (oral)<br>Drink with vitamins,<br>minerals, proteins,<br>and amino acids |
| 11:00 a.m. | | Flumazenil 2 mg per day | |

TABLE 15-continued

Treatment Protocol Followed During Hospitalization.

| TIME | DAY OF ADMISSION | DAY 2 | DAY 3 (DISCHARGE) |
|---|---|---|---|
| 1:00 p.m. | Clomethiazole 192 mg Vitamin B Complex Piracetam 3 g (oral) | | |
| 4:30 p.m. | Flumazenil 2 mg per day | | |
| 7:30 p.m. | Vitamin B Complex | Vitamin B Complex Disulfiram 250 mg | |
| 9:30 p.m. | Clomethiazole 384 mg | Clomethiazole 384 mg | |

Flumazenil was administered at a dose of 0.2 mg every 3 minutes (up to a total of 2 mg/day). This quantity per dose was established to minimize the adverse side effects associated with withdrawal or interactions with other pharmaceuticals or psychopathologies.

Patients who presented marked anxiety were administered an additional dose of 192 mg of clomethiazole 30 minutes before administration of flumazenil.

Before discharge from the hospital, the following medications were prescribed:

Vitamin B complex: 1 month with one dose during breakfast and one dose during lunch.

Piracetam, or a medicament that is pharmacologically equivalent, 3 g for 1 week with one dose during breakfast and 800 mg for 1 month with one dose during breakfast and one dose during lunch;

Fluoxetine 20 mg for 2 months with one dose during breakfast;

Clomethiazole 192 mg for 1 week with one dose during breakfast and one dose during dinner and a subsequent elimination of dose during the second week;

Disulfuram 250 mg with one dose during breakfast.

As part of the treatment program, the patients were instructed to attend the outpatient treatment center for 9 months with decreasing frequency [once a week for the first three months, once every two weeks during the second three months, and once a month during the third three months].

Likewise, a semi-structured follow-up of cognitive behavior therapy was implemented. Individual and family psychotherapy was focused on 4 major interventions (cognitive restructuring, work therapy, prevention of relapse, and stress reduction) aimed at rehabilitating the social, family, work, personal and leisure life of the patient.

1.2 Results

Of the 64 patients treated, in 3 cases, the first administration of flumazenil was interrupted and postponed to the following day: one of them, who was obviously intoxicated with alcohol, demonstrated a distressing increase in confusion, another had a significant increase in distal tremors, and the other, who was also addicted to benzodiazepines, demonstrated a significant increase in anxiety. Another group of 3 patients received the first dose of flumazenil under sedation with propofol in the intensive care unit.

Approximately 10% of the patients suffered headache during or immediately following the administration of flumazenil, which disappeared after a few minutes, or after administration of metamizole magnesium.

1.3 Results after the First Administration of Flumazenil

The CIWA-A scoring of 55 patients showed that: 47.3% had a significant reduction (t: −7.713; p<0.000); 40.0% experienced no change; and 12.7% had a significant increase (t: 2.511; p<0.046) [in the three cases presenting the greatest increase, the treatment was discontinued].

The heart rate values of 55 patients showed that: 50.9% had a significant reduction (t: −8.820; p<0.000); 40.0% experienced no change; and 9.1% had a significant increase (t: 4.750; p<0.009).

The systolic blood pressure values of 53 patients showed that: 47.2% had a significant reduction (t: −9.908; p<0.000); 37.7% experienced no change; and 15.1% had a significant increase (t: 4.314; p<0.004).

The diastolic blood pressure values of 53 patients showed that: 34% had a significant reduction (t: −9.220; p<0.000); 47.2% experienced no change; and 18.9% had a significant increase (t: 5.511; p<0.000).

1.4 Results after the Second Administration of Flumazenil

The CIWA-A scoring of 58 patients showed that: 36.2% had a significant reduction (t: −5.363; p<0.000); 55.2% experienced no change; and 8.6% had a significant increase (t: 4.000; p<0.016).

The heart rate values of 55 patients showed that: 41.8% had a significant reduction (t: −8.523; p<0.000); and 58.2% experienced no change.

The systolic blood pressure values of 56 patients showed that: 28.6 had a significant reduction (t: −7.596; p<0.000); 55.4% experienced no change; and 16.1% had a significant increase (t: 4.612; p<0.002).

The diastolic blood pressure values of 56 patients showed that: 28.6% had a significant reduction (t: −6.325; p<0.000); 51.8% experienced no change (n=29); and 19.6% had a significant increase (t: 6.640; p<0.000).

Table 16 statistically summarizes the results obtained before and after the treatment (at the end of 18 hours). Table 17 summarizes the follow-up data.

TABLE 16

Statistical Summary of Results Obtained
Before and After Treatment

|  | Mean (M) | | No. of Samples | | Standard Deviation (SD) | | Mean Error | | Student's T Factor | | Significance | |
|---|---|---|---|---|---|---|---|---|---|---|---|---|
|  | BT* | AT** | BT | AT | BT | AT | BT | AT | BT | AT | BT | AT |
| CIWA-A | 4.13 | .76 | 54 | 54 | 4.28 | 1.52 | 0.58 | 0.21 | 6.19 | | .002 | |
| Systolic Blood Pressure | 135.2 | 126.67 | 51 | 51 | 18.22 | 13.99 | 2.55 | 1.96 | 5.256 | | 0.0 | |
| Diastolic Blood Pressure | 86.27 | 82.75 | 51 | 51 | 10.76 | 9.13 | 1.51 | 1.28 | 3.273 | | .002 | |
| Heart Rate | 81.42 | 75.02 | 53 | 53 | 13.83 | 9.93 | 1.9 | 1.36 | 4.273 | | 0.0 | |

*Before Treatment,
**After Treatment

TABLE 17

Summary of Follow-Up Data

| | TIME | | | |
|---|---|---|---|---|
| | Month 1 | Month 3 | Month 6 | Month 9 |
| (% N) | 67.2/43 | 34.4/22 | 18.8/12 | 12.5/8 |
| Therapy and Disulfiram | 95.3% | 86.4% | 75% | 75% |
| Therapy without Disulfiram | 4.5% | | | 12.5% |
| Dropouts | 4.7% | 9.1% | 25% | 12.5% |

The psychophysiological functions such as appetite and sleep were regained very rapidly during hospitalization. The second day of hospitalization, the patients were permitted to spend a few hours outside the clinic during the afternoon. Some patients had dinner outside the clinic. The most striking result is the spontaneous verbal report from the majority of the patients concerning the absence of anxiety and of the desire to drink alcohol.

Example 2

Improved Methodology for the Administration of Flumazenil to Treat Alcohol Dependency Before starting the protocol, the patients underwent a complete medical and psychological examination. The monitoring of the patients included a complete blood count, a biochemical profile [creatinine, glucose, blood urea nitrogen (BUN), cholesterol (HDL and LDL), triglycerides, alkaline phosphatase, LDH (lactic dehydrogenase) and total proteins], hepatic function tests [GOT, GPT, GGT, bilirubin), electrocardiogram and, if need be, pregnancy test and x-ray examination. The exclusion criteria applied included acute or uncompensated illnesses, as well as the taking of any drug contraindicated with flumazenil. No patient was excluded after the pre-admission interview and the tests performed.

In addition, patients diagnosed with a psychotic disorder received anti-psychotic medication. Patients diagnosed with arterial hypertension are prescribed the appropriate medication or instructed to continue with any existing medication.

Patients were then intravenously administered 0.1 mg of flumazenil every 3 minutes for two administrations. If the patient did not experience any discomfort, then the dosage was increased up to 0.3 mg every 2 minutes. The total dosage of flumazenil administered was up to 3.0 mg per day for alcohol dependency over the course of the treatment.

Patients were also administered amino acids, nutrients, and vitamins. Non-addictive sedatives were also administered in order to reduce patient stress and/or discomfort.

Following administration of the protocol, patients underwent 6 to 24 months of outpatient therapy (for the first two months, once a week; the next four months, every two weeks; the next six months, once a month; and the last twelve months, once every two months). Depending on the patient, the outpatient treatment included cognitive behavioral semi-structured follow-up, such as individual and family psychotherapy that may include cognitive restructuring, network therapy, relapse prevention and stress reduction.

Example 3

Improved Methodology for the Administration of Flumazenil to Treat Alcohol Dependency In accordance with this embodiment of the present invention, as related to such example, a protocol for the treatment of alcohol cravings is described in the table below:

| | Time | | |
|---|---|---|---|
| | Admission Day | Day 2 | Day 3 - Discharge |
| Pre-Procedure (AM) | Atarax (sedative) - 50 mg (1-2 hour pre-procedure). May repeat with 25 mg for anxiety if needed. Fortified Vitamin B complex. Protein Drink. | Atarax (sedative) - 50 mg (1-2 hour pre-procedure). May repeat with 25 mg for anxiety if needed. Fortified Vitamin B complex. Protein Drink. | Fortified Vitamin B complex. Protein Drink. |
| Procedure | Flumazenil 2 mg per day | Flumazenil 2 mg per day | |

-continued

| | Time | | |
|---|---|---|---|
| | Admission Day | Day 2 | Day 3 - Discharge |
| Post-Procedure (PM) | Atarax 50 mg. at bedtime may repeat with 25 mg. as needed for sleep. | Atarax 50 mg. at bedtime may repeat with 25 mg. as needed for sleep. | |

At discharge, the following may be administered: disulfuram 250 mg., daily for six months; glutamic acid, 500 mg., once daily for one day, twice daily for one day, then three times daily for two weeks; vitamin B complex daily; and Atarax, 50 mg. at bedtime for one week and then 25 mg. at bedtime for a week.

Example 4

Improved Methodology for the Administration of Flumazenil to Treat Cocaine Dependency Before starting the protocol, the patients underwent a complete medical and psychological examination. The monitoring of the patients included a complete blood count, a biochemical profile [creatinine, glucose, urea, cholesterol (HDL and LDL), triglycerides, alkaline phosphatase, LDH (lactic dehydrogenase) and total proteins], hepatic function tests [GOT, GPT, GGT, bilirubin], electrocardiogram and, if warranted, pregnancy test and x-ray examination. The exclusion criteria applied included acute or uncompensated illnesses, as well as the taking of any drug contraindicated with flumazenil. No patient was excluded after the pre-admission interview and the tests performed.

In addition, patients diagnosed with a psychotic disorder received anti-psychotic medication. Patients diagnosed with arterial hypertension were prescribed with the appropriate medication or instructed to continue with any existing medication.

Patients were administered 0.1 mg of flumazenil every 3 minutes for two administrations. If the patient did not experience any discomfort, the dosage was increased up to 0.3 mg every 2 minutes. The total dosage of flumazenil administered was up to 3 mg per day over the course of the treatment.

Patients were also selectively administered amino acids, nutrients, and vitamins. Non-addictive sedatives were also administered in order to reduce patient stress and/or discomfort. Following administration of the protocol, patients underwent 6 to 24 months of outpatient therapy (for the first two months, once a week; the next four months, every two weeks; the next six months, once a month; and the last twelve months, once every two months). Depending on the patient, the outpatient treatment included cognitive behavioral semi-structured follow-, such as individual and family psychotherapy that may include cognitive restructuring, network therapy, relapse prevention and stress reduction.

Example 5

Improved Methodology for the Administration of Flumazenil to Treat Cocaine Dependency In accordance with this embodiment of the present invention, as related to such example, a protocol for the treatment of cravings for cocaine is described in the table below:

| | Time | | |
|---|---|---|---|
| | Admission Day | Day 2 | Day 3 - Discharge |
| Pre-Procedure (AM) | Atarax (sedative) - 50 mg (1-2 hour pre-procedure). May repeat with 25 mg for anxiety if needed. Fortified Vitamin B complex. Protein Drink. | Atarax (sedative) - 50 mg (1-2 hour pre-procedure). May repeat with 25 mg for anxiety if needed. Fortified Vitamin B complex. Protein Drink. | Fortified Vitamin B complex. Protein Drink. |
| Procedure | Flumazenil 2 mg per day | Flumazenil 2 mg per day | |
| Post-Procedure (PM) | Atarax 50 mg. at bedtime may repeat with 25 mg. as needed for sleep. | Atarax 50 mg. at bedtime may repeat with 25 mg. as needed for sleep. | |

At discharge, the following may be administered: Neurontin 400 mg. daily for one day (at morning), then two times daily for one day (morning and bedtime), then three times daily and continuing for six months (decrease by 400 mg. weekly in order to discontinue); glutamic acid, 500 mg., once daily for one day, twice daily for one day, then three times daily for two weeks; vitamin B complex daily; and Atarax, 50 mg. at bedtime for one week and then 25 mg. at bedtime for a week.

Example 6

Enhanced Methodology for the Administration of Flumazenil for the Treatment of Alcohol Withdrawal The following example is of an embodiment of an enhanced protocol for the administration of flumazenil for the treatment of alcohol dependency. The enhanced protocol is implemented to concentrate targeting of $GABA_A$ Receptor Ionophore Complex. The embodiment employs a CIWA-based algorithm for 1) triage of patients in need of acute medical detoxification and 2) to provide symptom-based tracking throughout acute phase of the protocol treatment. The enhanced protocol also alleviates withdrawal related sleep disturbance and anxiety. In addition, the enhanced protocol supplies key co-factors that synergistically enhance GABA tone and transmission.

In the exemplary enhanced protocol for treating alcohol withdrawal, a patient undergoes the aforementioned pre-treatment regimen. On day 1 of treatment, the patient receives flumazenil via an intravenous infusion, ultimately delivering a total amount of 2 mg per dosing interval. The patient further receives 50 mg of hydroxyzine during the day and 50 mg of hydroxyzine at bedtime or in the evening. The patient further receives fortified vitamin B complex and Gabapentin at a dose of 300 mg.

On day 2 of treatment, the patient receives flumazenil via an intravenous infusion, ultimately delivering a total amount of 2 mg per dosing interval. The patient further receives 50 mg of hydroxyzine during the day and 50 mg of hydroxyzine at bed or in the evening. The patient further receives fortified vitamin B complex daily and Gabapentin at a dose of 300 mg in the afternoon and evening or at bedtime.

After discharge, for days one and two, the patient receives 50 mg of hydroxzine at bedtime or in the evening. For 30 days, the patient receives Gabapentin at a dose of 900 mg in the afternoon and evening or at bedtime then titrating down to 0. For one week, the patient also receives vitamin B complex daily.

Example 7

Enhanced Methodology for the Administration of Flumazenil for the Treatment of Alcohol Withdrawal In a third exemplary methodology for treating alcohol withdrawal, a patient undergoes a pre-treatment procedure that includes a CIWA assessment and the administration of hydroxyzine at a dose of 50 mg. On day one of treatment, a first infusion is administered to the patient. The first infusion includes vitamin B1, vitamin B6, vitamin B12, and vitamin B complex and 2 mg of flumazenil over a period of 2 hours. After the first infusion, the patient undergoes a post-treatment procedure, typically in the late afternoon to evening that includes a CIWA assessment, the administration of Gabapentin at a dose of 300 mg, and the administration of hydroxyzine at a dose of 50 mg in the evening or bedtime.

On day two of treatment, a patient undergoes a pre-treatment procedure that includes a CIWA assessment and the administration of hydroxyzine at a dose of 50 mg. A second infusion is then administered to the patient. The second infusion includes vitamin B1, vitamin B6, vitamin B12, and vitamin B complex and 2 mg of flumazenil over a period of 2 hours. After the second infusion, the patient undergoes a post-treatment procedure, typically in the late afternoon to evening that includes a CIWA assessment, the administration of Gabapentin at a dose of 300 mg, and the administration of hydroxyzine at a dose of 50 mg in the evening or bedtime.

After discharge, the patient is monitored based on the CIWA assessment and the patient's medical condition. Optionally, prior to discharge, the patient undergoes a third day of treatment that is similar to day 2, if warranted by the patient's medical condition and/or CIWA assessment.

At discharge, the patient is given 50 mg of hydroxyzine on days 1 and 2 at bedtime. The patient is also given gabapentin in the following amounts: 300 mg on day 1; 600 mg on day 2; and on days 3-30, 900 mg titrated down to zero. The patient is also given an Oral Vitamin B 100 complex daily for one week.

Example 8

Enhanced Methodology for the Administration of Flumazenil for the Treatment of Stimulant Withdrawal The following example is of an embodiment of an enhanced methodology for the administration of flumazenil for the treatment of psychostimulant dependency. The enhanced methodology is implemented to concentrate targeting of $GABA_A$ Receptor Ionophore Complex. The embodiment allows for streamlining of nutritional components. In addition, the enhanced methodology also alleviates withdrawal related sleep disturbance and anxiety. The enhanced methodology also supplies key co-factors that synergistically enhance GABA tone and transmission.

In a first exemplary enhanced methodology for treating stimulant withdrawal, a patient undergoes the aforementioned pre-treatment regimen. On days 1, 2 and 3 of treatment, the patient receives flumazenil via an intravenous infusion, ultimately delivering a total amount of 2 mg per dosing interval. The patient further receives 50 mg of hydroxyzine twice daily plus or minus 25 mg as may be required. The patient further receives fortified vitamin B complex daily and a protein supplement drink daily in the morning. This regimen, preferably days 1 and 2 only, is repeated after three weeks.

After discharge, for one week, the patient receives 50 mg of hydroxyzine at bedtime or for sleep and, for a subsequent week, the patient receives 25 mg of hydroxyzine at bedtime or for sleep. For two weeks, the patient also receives glutamine titrated up to 1500 mg per day and fortified vitamin B complex daily. The patient further receives Gabapentin titrated up to 1200 mg per day for six months. This regimen is interrupted for a second round of treatments, as described above, after three weeks have elapsed from the first round of treatments and restarted thereafter.

Example 9

Enhanced Methodology for the Administration of Flumazenil for the Treatment of Stimulant Withdrawal In a second exemplary methodology for treating stimulant withdrawal, a patient undergoes the aforementioned pre-treatment regimen. On days 1, 2 and 3 of treatment, the patient receives flumazenil via an intravenous infusion, ultimately delivering a total amount of 2 mg per dosing interval. The patient further receives 50 mg of hydroxyzine. The patient further receives fortified vitamin B complex daily and Gabapentin at a dose of 300 mg. This regimen, preferably days 1 and 2 only, is repeated after three weeks.

After discharge, the patient receives Gabapentin titrated up to 400 mg per day for 30 days, decreasing to 0. The patient also receives fortified vitamin B 100 complex daily and a plurality of amino acid supplements. This regimen is interrupted for a second round of treatments, as described above, after three weeks have elapsed from the first round of treatments and restarted thereafter.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention is not to be limited to the details given herein, but may be modified within the scope of the appended claims.

I claim:

1. A method for the treatment of psychological dependence on methamphetamine in a human patient having psychological dependence on methamphetamine, wherein the patient is not undergoing withdrawal, comprising the sequential steps of: optionally administering about 50 mg of hydroxyzine to the patient; administering to the patient a therapeutically effective amount of a composition comprising flumazenil in a pharmaceutically acceptable carrier, wherein the therapeutically effective amount of flumazenil is between about 0.5 and about 10 mg/day; and, administering gabapentin to the patient in an amount of about 300 mg to about 600 mg.

2. The method of claim 1, further comprising:
evaluating the patient via a pre-treatment regimen;
monitoring the patient during treatment;
prescribing the patient a therapeutic compound in addition to the flumazenil and the gabapentin; and
prescribing the patient an outpatient regimen.

3. The method of claim 1 wherein the therapeutically effective amount of flumazenil is less than 3 mg/day and is delivered in individual doses of 0.4 mg or less over a period of 20 minutes or less.

4. The method of claim 2, wherein the therapeutic compound includes at least one of a fortified vitamin B complex, hydroxyzine, or protein supplement drink.

5. The method of claim 2 wherein the outpatient regimen includes at least one of diet, exercise, cognitive therapy, or providing a pharmaceutical composition.

6. The method of claim 5 wherein the pharmaceutical composition includes at least one of hydroxyzine, glutamine, fortified vitamin B complex, or an amino acid supplement.

7. The method of claim 2 wherein the steps of administering a therapeutically effective amount of the composition comprising flumazenil in the pharmaceutically acceptable carrier to the patient; monitoring the patient during treatment; and prescribing the patient the therapeutic compound in addition to the flumazenil, are repeated three weeks after initial treatment.

* * * * *